United States Patent [19]

Matsuda et al.

[11] Patent Number: 5,654,420

[45] Date of Patent: Aug. 5, 1997

[54] PROCESS FOR PREPARING 2'-CYANO PYRIMIDINE NUCLEOSIDE COMPOUNDS

[75] Inventors: Akira Matsuda, Sapporo, Japan; Tohru Ueda, deceased, late of Sapporo, Japan, by Sumiko Ueda, legal representative

[73] Assignee: Sankyo Company, Limited, Tokyo, Japan

[21] Appl. No.: 457,510

[22] Filed: Jun. 1, 1995

Related U.S. Application Data

[62] Division of Ser. No. 301,720, Sep. 7, 1994, which is a continuation of Ser. No. 989,719, filed as PCT/JP91/00797, Jun. 13, 1991 published as WO91/19713, Dec. 26, 1991, abandoned.

[30] Foreign Application Priority Data

Jun. 15, 1990 [JP] Japan ............................ 2-156688

[51] Int. Cl.$^6$ ............................ C07H 19/06; C07H 19/09
[52] U.S. Cl. ................ 536/27.4; 536/28.1; 536/28.2; 536/28.4; 536/28.5; 536/28.52; 536/28.53; 536/28.54
[58] Field of Search ................ 536/28.1, 28.4, 536/28.5, 28.51, 28.52, 28.53, 28.54, 28.55, 27.4, 28.2

[56] References Cited

FOREIGN PATENT DOCUMENTS 2 007 094  6/1989  Spain .

OTHER PUBLICATIONS

Dieter Häbich, et al, "Synthesis of 3'-Cyano-3'-deoxy-β-D-arabino-nucleosides", 1988, pp. 943–947, *Synthesis*.
Dong Yu et al, "Synthesis of 3'-Cyano-2', 3'-dideoyadenosine and 2', 3'-Dideoxy-3'-formyladenosine", 1989, pp. 3240–3342, *J. Org. Chem*.
Matsuda et al, *Chemical Abstracts*, "Synthesis of a New Patent Antitumor Nucleoside-2'-C-cyano-2'-deoxy-1-β-D-arabinofuransyl-cytosine", 115 (3): 29817a (1991).
A. Matsuda et al, "Nucleosides and Nucleotides. 100.2'-C-Cyano-2'-deoxy-1-β-D-arabinofuransyl-cytosine (CNDAE): Design of a Potential Mechanism-Based DNA-Srrand Breaking Antineoplastic Nucleoside", *J. Med. Chem.*, vol. 34 (9), 2917–2919, Sep. 1991.

T. Beardsley, "A War Not Won", *Scientific American*, (Jan. 1994), vol. 270, No. 1, 130–138.

*Primary Examiner*—James O. Wilson
*Attorney, Agent, or Firm*—Frishauf, Holtz, Goodman, Langer & Chick, P.C.

[57] ABSTRACT

A process for preparing a compound of the formula:

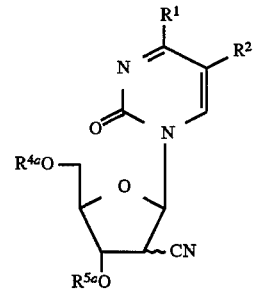

wherein $R^1$ is a hydroxyl or an amino which may optionally be substituted; $R^2$ is a hydrogen or a $C_1$–$C_4$ alkyl; and $R^{4a}$ and $R^{5a}$ together represent a group of the formula: —$R^6R^7$Si—O—Si$R^{6'}R^{7'}$, wherein $R^6$, $R^7$, $R^{6'}$ and $R^{7'}$ are the same or different and each is a $C_1$–$C_4$ alkyl, which process comprises reacting a reducing agent and a cyanolating agent with a compound of the formula:

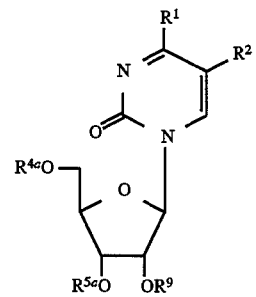

wherein $R^9$ is an alkoxythiocarbonyl having a $C_1$–$C_4$ alkyl or an arylthiocarbonyl having a $C_6$–$C_{10}$ aryl.

19 Claims, No Drawings

PROCESS FOR PREPARING 2'-CYANO PYRIMIDINE NUCLEOSIDE COMPOUNDS

This is a division of application Ser. No. 08/301,720 filed Sep. 7, 1994, which is a continuation of application Ser. No. 07/989,719 filed Dec. 14, 1992 (abandoned), which is a continuation of International Application No. PCT/JP91/00797 filed Jun. 13, 1991 published as WO91/19713, Dec. 26, 1991.

TECHNICAL FIELD

The present invention relates to novel pyrimidine nucleoside derivatives having excellent antitumor activities.

BACKGROUND ART

As the commercially available antitumor agents of pyrimidine series metabolism antagonistic agents, 5-fluorouracil (Duschinsky, R., et al., J. Am. Chem. Soc., 79, 4559 (1957)), Tegafur (Hiller, SA., et al., Dokl. Akad. Nauk USSR, 176, 332 (1967)), UFT (Fujii, S., et al., Gann, 69, 763 (1978)), Carmofur (Hoshi, A., et al., Gann, 67, 725 (1976)), Doxyfluridine (Cook, A. F., et al., J. Med. Chem., 22, 1330 (1979)), Cytarabine (Evance, J. S., et al., Proc. Soc. Exp. Bio. Med., 106, 350 (1961)), Ancytabine (Hoshi, A., et al., Gann, 63, 353, (1972)), Enocytabine (Aoshima, M., et al., Cancer Res., 36, 2726 (1976)), etc. are so far known.

As the pyrimidine mononucleoside having a cyano group at the ribose moiety, 3'-cyanothymine nucleoside and 3'-cyanouracil nucleoside derivatives are only known (Japanese Unexamined Patent Publication Nos. Hei-2-83392, Hei-2-104586 and Hei-2-503002).

DISCLOSURE OF THE INVENTION

The present inventors made extensive studies for a long period of time with a view to developing an absolutely novel antimetabolites which is superior to the existing antitumor agents described above to find that compounds wherein a cyano group is introduced to the 2'-position of the sugar moiety of pyrimidine series nucleosides have strong antitumor activities to various tumor systems and such compounds can be intermediates for producing such compounds having strong antitumor activities, and they accomplished the present invention.

CONSTITUTION OF THE INVENTION

The novel pyrimidine nucleoside derivatives having strong antitumor activities according to the present invention are compounds having the general formula:

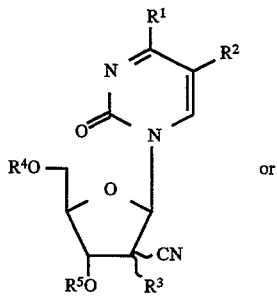

(1)

or the general formula:

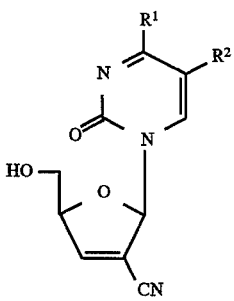

(2)

and pharmacologically acceptable nontoxic salts thereof.

In the above general formulae (1) and (2), $R^1$ represents a hydroxyl group or an amino group which may optionally have a substituent selected from the following group A or B: $R^2$ represents a hydrogen atom or an alkyl group having 1 to 4 carbon atoms; $R^3$ represents a hydrogen atom or a hydroxyl group; and $R^4$ and $R^5$ each represent a hydrogen atom or together may form a group —$R^6R^7$Si—O—Si$R^{6'}R^{7'}$—(wherein $R^6$, $R^7$, $R^{6'}$ and $R^{7'}$ may be the same or different from one another and each represent an alkyl group having 1 to 4 carbon atoms).

Group A

Aliphatic acyl having 1 to 4 carbon atoms and aromatic acyl having 7 to 11 carbon atoms which may have a substituent on the ring.

Group B

Alkoxycarbonyl having a $C_1$–$C_4$ alkyl, alkenyloxycarbonyl having a $C_2$–$C_4$ alkenyl, aralkyloxycarbonyl having 8 to 12 carbon atoms which may have a substituent on the ring.

The aliphatic acyl having 1 to 4 carbon atoms as the substituent $R^1$ mentioned above includes formyl, acetyl, propionyl, butyryl and isopropionyl, preferably an aliphatic acyl having 1 to 2 carbon atoms. The aromatic acyl having 7 to 11 carbon atoms includes benzoyl, α-naphthoyl and β-naphthoyl, preferably benzoyl. The substituent moiety on the aromatic ring includes an alkyl having 1 to 4 carbon atoms, an alkoxy having 1 to 4 carbon atoms and an aliphatic acyl having 1 to 4 carbon atoms, preferably methyl, ethyl, methoxy, ethoxy and acetyl groups. The alkyl moiety of the alkoxycarbonyl having a $C_1$–$C_4$ alkyl group includes methyl, ethyl, n-propyl, isopropyl, n-butyl, isobutyl and t-butyl, preferably methyl and t-butyl. The alkenyl moiety of the alkenyloxycarbonyl having a $C_2$–$C_4$ alkenyl includes vinyl, allyl, isopropenyl, 1-butenyl and 2-butenyl, preferably allyl. The aralkyl moiety of the aralkyloxycarbonyl having 8 to 12 carbon atoms includes benzyl, phenethyl, α-naphthylmethyl and β-naphthylethyl, preferably benzyl. The substituent on the aromatic ring includes an alkyl having 1 to 4 carbon atoms, an alkoxy having 1 to 4 carbon atoms and an aliphatic acyloxy having 1 to 4 carbon atoms, preferably methyl, ethyl, methoxy, ethoxy and acetoxy.

$R^1$ mentioned above preferably includes a hydroxyl group, an amino group, an amino group substituted with a $C_1$–$C_2$ aliphatic acyl, an amino group substituted with an aromatic acyl having 7 carbon atoms which may have a substituent on the ring, an amino group substituted with an alkoxycarbonyl having a $C_1$–$C_4$ alkyl, an amino group substituted with an alkenyloxycarbonyl having a $C_3$ alkenyl, an amino group substituted with an aralkyloxycarbonyl having 8 carbon atoms which may have a substituent on the ring, more preferably a hydroxyl group, an amino group, an amino group substituted with an aliphatic acyl having 1 to 2 carbon atoms, an amino group substituted with an aromatic acyl having 7 carbon atoms, most preferably a hydroxyl group and an amino group.

The R² alkyl group having 1 to 4 carbon atoms includes methyl, ethyl, propyl, isopropyl, butyl, isobutyl and t-butyl groups, preferably a methyl group.

R² mentioned above preferably includes a hydrogen atom and a methyl group.

The $R^6$, $R^{6'}$, $R^7$ or $R^{7'}$ alkyl group having 1 to 4 carbon atoms includes methyl, ethyl, propyl, Isopropyl, butyl, isobutyl and t-butyl groups, preferably isopropyl group.

$R^4$ and $R^5$ mentioned above each are a hydrogen atom or together form a tetramethyldisiloxdiyl group, a tetraethyldisiloxdiyl group, a tetrapropyldisiloxdiyl group, a tetraisopropyldisiloxdiyl group, a tetrabutyldisiloxdiyl group, a diethyldiisopropyldisiloxdiyl group or a dibutyldiisopropyldisiloxdiyl group, preferably a hydrogen atom or a tetraisopropyldisiloxdiyl group, more preferably a hydrogen atom.

The pharmacologically acceptable nontoxic salts of the compounds having the above general formulae (1) or (2) of the present invention can be exemplified by salts of mineral acids such as hydrochloride, hydrobromide and sulfate, organic sulfonates such as methane sulfonate and benzene sulfonate, aliphatic carboxylates such as acetate, propionate, butyrate, and caproate and aromatic carboxylates such as benzoate.

Among those salts, the salts of mineral acids (particularly hydrochloric acid) and aliphatic carboxylates (particularly acetic acid) are preferred.

In Compounds (1) and (2), there may preferably be mentioned:

1) Compounds wherein $R^1$ represents a hydroxyl group or an amino group which may have a substituent selected from the following group A' or B'; $R^2$ represents a hydrogen atom or an alkyl group having 1 to 4 carbon atoms: $R^3$ represents a hydrogen atom or a hydroxyl group; and $R^4$ and $R^5$ each represent a hydrogen atom or together form a tetraisopropyldisiloxdiyl group.

Group A'

An aliphatic acyl having 1 to 2 carbon atoms and an aromatic acyl having 7 carbon atoms which may have a substituent on the ring.

Group B'

An alkoxycarbonyl having a $C_1$–$C_4$ alkyl, an alkenyloxycarbonyl having a $C_3$ alkenyl and an aralkyloxycarbonyl having 8 carbon atoms which may have a substituent on the ring.

2) Compounds wherein $R^1$ represents a hydroxyl group or an amino group which may have a substituent selected from the following group A'; $R^2$ represents a hydrogen atom or a methyl group; $R^3$ represents a hydrogen atom or a hydroxyl group; and $R^4$ and $R^5$ each represent a hydrogen atom.

Group A'

An aliphatic acyl having 1 to 2 carbon atoms and an aromatic acyl having 7 carbon atoms which may have a substituent on the ring.

3) Compounds wherein $R^1$ represents a hydroxyl group or an amino group; $R^2$ represents a hydrogen atom or a methyl group; $R^3$ represents a hydrogen atom or a hydroxyl group; and $R^4$ and $R^5$ each represent a hydrogen atom.

Compounds (1) and (2) of the present invention can typically be exemplified by those listed in Table 1, Table 2 and Table 3, but the present invention is not limited thereto.

Incidentally, Table 1, Table 2 and Table 3 show compounds of the formula A, compounds of the formula B and compounds of the formula C, respectively. In Table 1, Table 2 and Table 3, Et, Pr, tBu, AL, Ac, Bz, BzpMe, BzpOMe, By and BypOAc mean an ethyl group, propyl group, tert-butyl group, allyl group, acetyl group, benzoyl group, p-methylbenzoyl group, p-methoxybenzoyl group, benzyl group and p-acetoxybenzyl group, respectively.

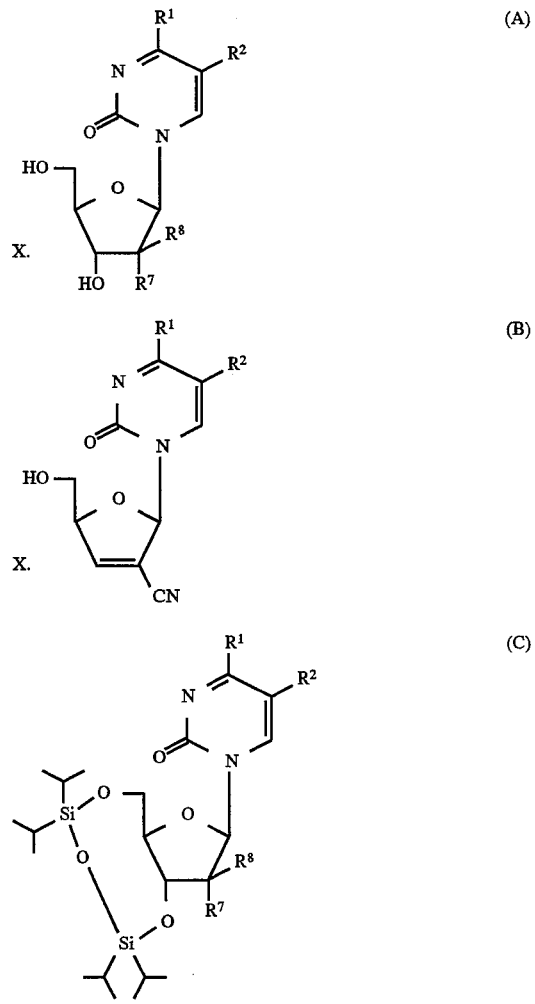

TABLE 1

| No. | $R^1$ | $R^2$ | $R^7$ | $R^8$ | X |
|---|---|---|---|---|---|
| 1-1 | NH₂ | H | H | CN | — |
| 1-2 | NH₂ | CH₃ | H | CN | — |
| 1-3 | NH₂ | CH₃CH₂ | H | CN | — |
| 1-4 | NH₂ | CH₃(CH₂)₂ | H | CN | — |
| 1-5 | NH₂ | (CH₃)₂CH | H | CN | — |
| 1-6 | NH₂ | CH₃(CH₂)₃ | H | CN | — |
| 1-7 | NH₂ | H | H | CN | HCl |
| 1-8 | NH₂ | CH₃ | H | CN | HCl |
| 1-9 | NH₂ | CH₃CH₂ | H | CN | HCl |
| 1-10 | NH₂ | CH₃(CH₂)₂ | H | CN | HCl |
| 1-11 | NH₂ | (CH₃)₂CH | H | CN | HCl |
| 1-12 | NH₂ | CH₃(CH₂)₃ | H | CN | HCl |
| 1-13 | OH | H | H | CN | — |
| 1-14 | OH | CH₃ | H | CN | — |
| 1-15 | OH | CH₃CH₂ | H | CN | — |
| 1-16 | OH | CH₃(CH₂)₂ | H | CN | — |
| 1-17 | OH | (CH₃)₂CH | H | CN | — |
| 1-18 | OH | CH₃(CH₂)₃ | H | CN | — |
| 1-19 | NH₂ | H | CN | OH | — |
| 1-20 | NH₂ | CH₃ | CN | OH | — |
| 1-21 | NH₂ | CH₃CH₂ | CN | OH | — |
| 1-22 | NH₂ | CH₃(CH₂)₂ | CN | OH | — |
| 1-23 | NH₂ | (CH₃)₂CH | CN | OH | — |
| 1-24 | NH₂ | CH₃(CH₂)₃ | CN | OH | — |
| 1-25 | NH₂ | H | CN | OH | HCl |
| 1-26 | NH₂ | CH₃ | CN | OH | HCl |

TABLE 1-continued

| No. | R$^1$ | R$^2$ | R$^7$ | R$^8$ | X |
|---|---|---|---|---|---|
| 1-27 | NH$_2$ | CH$_3$CH$_2$ | CN | OH | HCl |
| 1-28 | NH$_2$ | CH$_3$(CH$_2$)$_2$ | CN | OH | HCl |
| 1-29 | NH$_2$ | (CH$_3$)$_2$CH | CN | OH | HCl |
| 1-30 | NH$_2$ | CH$_3$(CH$_2$)$_3$ | CN | OH | HCl |
| 1-31 | OH | H | CN | OH | — |
| 1-32 | OH | CH$_3$ | CN | OH | — |
| 1-33 | OH | CH$_3$CH$_2$ | CN | OH | — |
| 1-34 | OH | CH$_3$(CH$_2$)$_2$ | CN | OH | — |
| 1-35 | OH | (CH$_3$)$_2$CH | CN | OH | — |
| 1-36 | OH | CH$_3$(CH$_2$)$_3$ | CN | OH | — |
| 1-37 | NH$_2$ | H | CN | H | — |
| 1-38 | NH$_2$ | CH$_3$ | CN | H | — |
| 1-39 | NH$_2$ | CH$_3$CH$_2$ | CN | H | — |
| 1-40 | NH$_2$ | CH$_3$(CH$_2$)$_2$ | CN | H | — |
| 1-41 | NH$_2$ | (CH$_3$)$_2$CH | CN | H | — |
| 1-42 | NH$_2$ | CH$_3$(CH$_2$)$_3$ | CN | H | — |
| 1-43 | NH$_2$ | H | CN | H | HCl |
| 1-44 | NH$_2$ | CH$_3$ | CN | H | HCl |
| 1-45 | NH$_2$ | CH$_3$CH$_2$ | CN | H | HCl |
| 1-46 | NH$_2$ | CH$_3$(CH$_2$)$_2$ | CN | H | HCl |
| 1-47 | NH$_2$ | (CH$_3$)$_2$CH | CN | H | HCl |
| 1-48 | NH$_2$ | CH$_3$(CH$_2$)$_3$ | CN | H | HCl |
| 1-49 | OH | H | CN | H | — |
| 1-50 | OH | CH$_3$ | CN | H | — |
| 1-51 | OH | CH$_3$CH$_2$ | CN | H | — |
| 1-52 | OH | CH$_3$(CH$_2$)$_2$ | CN | H | — |
| 1-53 | OH | (CH$_3$)$_2$CH | CN | H | — |
| 1-54 | OH | CH$_3$(CH$_2$)$_3$ | CN | H | — |
| 1-55 | NH$_2$ | H | OH | CN | — |
| 1-56 | NH$_2$ | CH$_3$ | OH | CN | — |
| 1-57 | NH$_2$ | CH$_3$CH$_2$ | OH | CN | — |
| 1-58 | NH$_2$ | CH$_3$(CH$_2$)$_2$ | OH | CN | — |
| 1-59 | NH$_2$ | (CH$_3$)$_2$CH | OH | CN | — |
| 1-60 | NH$_2$ | CH$_3$(CH$_2$)$_3$ | OH | CN | — |
| 1-61 | NH$_2$ | H | OH | CN | HCl |
| 1-62 | NH$_2$ | CH$_3$ | OH | CN | HCl |
| 1-63 | NH$_2$ | CH$_3$CH$_2$ | OH | CN | HCl |
| 1-64 | NH$_2$ | CH$_3$(CH$_2$)$_2$ | OH | CN | HCl |
| 1-65 | NH$_2$ | (CH$_3$)$_2$CH | OH | CN | HCl |
| 1-66 | NH$_2$ | CH$_3$(CH$_2$)$_3$ | OH | CN | HCl |
| 1-67 | OH | H | OH | CN | — |
| 1-68 | OH | CH$_3$ | OH | CN | — |
| 1-69 | OH | CH$_3$CH$_2$ | OH | CN | — |
| 1-70 | OH | CH$_3$(CH$_2$)$_2$ | OH | CN | — |
| 1-71 | OH | (CH$_3$)$_2$CH | OH | CN | — |
| 1-72 | OH | CH$_3$(CH$_2$)$_3$ | OH | CN | — |
| 1-73 | NHBz | H | H | CN | — |
| 1-74 | NHCOOtBu | H | H | CN | — |
| 1-75 | NHCOOBy | H | H | CN | — |
| 1-76 | NHCOOAL | H | H | CN | — |
| 1-77 | NHBz | CH$_3$ | H | CN | — |
| 1-78 | NHBz | CH$_3$CH$_2$ | H | CN | — |
| 1-79 | NHBz | CH$_3$(CH$_2$)$_2$ | H | CN | — |
| 1-80 | NHBz | (CH$_3$)$_2$CH | H | CN | — |
| 1-81 | NHBz | CH$_3$(CH$_2$)$_3$ | H | CN | — |
| 1-82 | NHBz | H | CN | H | — |
| 1-83 | NHBz | CH$_3$ | CN | H | — |
| 1-84 | NHBz | CH$_3$CH$_2$ | CN | H | — |
| 1-85 | NHBz | CH$_3$(CH$_2$)$_2$ | CN | H | — |
| 1-86 | NHBz | (CH$_3$)$_2$CH | CN | H | — |
| 1-87 | NHBz | CH$_3$(CH$_2$)$_3$ | CN | H | — |
| 1-88 | NHAc | H | H | CN | — |
| 1-89 | NHCOH | H | H | CN | — |
| 1-90 | NHCOEt | H | H | CN | — |
| 1-91 | NHCOPr | H | H | CN | — |
| 1-92 | NHAc | CH$_3$ | H | CN | — |
| 1-93 | NHAc | CH$_3$CH$_2$ | H | CN | — |
| 1-94 | NHAc | CH$_3$(CH$_2$)$_2$ | H | CN | — |
| 1-95 | NHAc | (CH$_3$)$_2$CH | H | CN | — |
| 1-96 | NHAc | CH$_3$(CH$_2$)$_3$ | H | CN | — |
| 1-97 | NHAc | H | OH | CN | — |
| 1-98 | NHAc | CH$_3$ | OH | CN | — |
| 1-99 | NHAc | CH$_3$CH$_2$ | OH | CN | — |
| 1-100 | NHAc | CH$_3$(CH$_2$)$_2$ | OH | CN | — |
| 1-101 | NHAc | (CH$_3$)$_2$CH | OH | CN | — |
| 1-102 | NHAc | CH$_3$(CH$_2$)$_3$ | OH | CN | — |
| 1-103 | NHAc | H | CN | H | — |
| 1-104 | NHAc | CH$_3$ | CN | H | — |
| 1-105 | NHAc | CH$_3$CH$_2$ | CN | H | — |
| 1-106 | NHAc | CH$_3$(CH$_2$)$_2$ | CN | H | — |
| 1-107 | NHAc | (CH$_3$)$_2$CH | CN | H | — |
| 1-108 | NHAc | CH$_3$(CH$_2$)$_3$ | CN | H | — |

TABLE 2

| No. | R$^1$ | R$^2$ | X |
|---|---|---|---|
| 2-1 | NH$_2$ | H | — |
| 2-2 | NH$_2$ | CH$_3$ | — |
| 2-3 | NH$_2$ | CH$_3$CH$_2$ | — |
| 2-4 | NH$_2$ | CH$_3$(CH$_2$)$_2$ | — |
| 2-5 | NH$_2$ | (CH$_3$)$_2$CH | — |
| 2-6 | NH$_2$ | CH$_3$(CH$_2$)$_3$ | — |
| 2-7 | NH$_2$ | H | HCl |
| 2-8 | NH$_2$ | CH$_3$ | HCl |
| 2-9 | NH$_2$ | CH$_3$CH$_2$ | HCl |
| 2-10 | NH$_2$ | CH$_3$(CH$_2$)$_2$ | HCl |
| 2-11 | NH$_2$ | (CH$_3$)$_2$CH | HCl |
| 2-12 | NH$_2$ | CH$_3$(CH$_2$)$_3$ | HCl |
| 2-13 | OH | H | — |
| 2-14 | OH | CH$_3$ | — |
| 2-15 | OH | CH$_3$CH$_2$ | — |
| 2-16 | OH | CH$_3$(CH$_2$)$_2$ | — |
| 2-17 | OH | (CH$_3$)$_2$CH | — |
| 2-18 | OH | CH$_3$(CH$_2$)$_3$ | — |
| 2-19 | NHAc | H | — |
| 2-20 | NHAc | CH$_3$ | — |
| 2-21 | NHAc | CH$_3$CH$_2$ | — |
| 2-22 | NHAc | CH$_3$(CH$_2$)$_2$ | — |
| 2-23 | NHAc | (CH$_3$)$_2$CH | — |
| 2-24 | NHAc | CH$_3$(CH$_2$)$_3$ | — |
| 2-25 | NHBzpMe | H | — |
| 2-26 | NHBzpOMe | CH$_3$ | — |
| 2-27 | NHCOOtBu | CH$_3$CH$_2$ | — |
| 2-28 | NHCOOBy | CH$_3$(CH$_2$)$_2$ | — |
| 2-29 | NHCOOAL | (CH$_3$)$_2$CH | — |
| 2-30 | NHCOOBypOAc | CH$_3$(CH$_2$)$_3$ | — |
| 2-31 | NHBz | H | — |
| 2-32 | NHBz | CH$_3$ | — |
| 2-33 | NHBz | CH$_3$CH$_2$ | — |
| 2-34 | NHBz | CH$_3$(CH$_2$)$_2$ | — |
| 2-35 | NHBz | (CH$_3$)$_2$CH | — |
| 2-36 | NHBz | CH$_3$(CH$_2$)$_3$ | — |
| 2-37 | NHAc | H | — |
| 2-38 | NHAc | CH$_3$ | — |
| 2-39 | NHAc | CH$_3$CH$_2$ | — |
| 2-40 | NHAc | CH$_3$(CH$_2$)$_2$ | — |
| 2-41 | NHAc | (CH$_3$)$_2$CH | — |
| 2-42 | NHAc | CH$_3$(CH$_2$)$_3$ | — |

TABLE 3

| No. | R$^1$ | R$^2$ | R$^7$ | R$^8$ | X |
|---|---|---|---|---|---|
| 3-1 | NH$_2$ | H | H | CN | — |
| 3-2 | NH$_2$ | CH$_3$ | H | CN | — |
| 3-3 | NH$_2$ | CH$_3$CH$_2$ | H | CN | — |
| 3-4 | NH$_2$ | CH$_3$(CH$_2$)$_2$ | H | CN | — |
| 3-5 | NH$_2$ | (CH$_3$)$_2$CH | H | CN | — |
| 3-6 | NH$_2$ | CH$_3$(CH$_2$)$_3$ | H | CN | — |
| 3-7 | OH | H | H | CN | — |
| 3-8 | OH | CH$_3$ | H | CN | — |
| 3-9 | OH | CH$_3$CH$_2$ | H | CN | — |
| 3-10 | OH | CH$_3$(CH$_2$)$_2$ | H | CN | — |
| 3-11 | OH | (CH$_3$)$_2$CH | H | CN | — |
| 3-12 | OH | CH$_3$(CH$_2$)$_3$ | H | CN | — |
| 3-13 | NH$_2$ | H | CN | OH | — |
| 3-14 | NH$_2$ | CH$_3$ | CN | OH | — |
| 3-15 | NH$_2$ | CH$_3$CH$_2$ | CN | OH | — |

TABLE 3-continued

| No. | R¹ | R² | R⁷ | R⁸ | X |
|---|---|---|---|---|---|
| 3-16 | $NH_2$ | $CH_3(CH_2)_2$ | CN | OH | — |
| 3-17 | $NH_2$ | $(CH_3)_2CH$ | CN | OH | — |
| 3-18 | $NH_2$ | $CH_3(CH_2)_3$ | CN | OH | — |
| 3-19 | OH | H | CN | OH | — |
| 3-20 | OH | $CH_3$ | CN | OH | — |
| 3-21 | OH | $CH_3CH_2$ | CN | OH | — |
| 3-22 | OH | $CH_3(CH_2)_2$ | CN | OH | — |
| 3-23 | OH | $(CH_3)_2CH$ | CN | OH | — |
| 3-24 | OH | $CH_3(CH_2)_3$ | CN | OH | — |
| 3-25 | $NH_2$ | H | CN | H | — |
| 3-26 | $NH_2$ | $CH_3$ | CN | H | — |
| 3-27 | $NH_2$ | $CH_3CH_2$ | CN | H | — |
| 3-28 | $NH_2$ | $CH_3(CH_2)_2$ | CN | H | — |
| 3-29 | $NH_2$ | $(CH_3)_2CH$ | CN | H | — |
| 3-30 | $NH_2$ | $CH_3(CH_2)_3$ | CN | H | — |
| 3-31 | OH | H | CN | H | — |
| 3-32 | OH | $CH_3$ | CN | H | — |
| 3-33 | OH | $CH_3CH_2$ | CN | H | — |
| 3-34 | OH | $CH_3(CH_2)_2$ | CN | H | — |
| 3-35 | OH | $(CH_3)_2CH$ | CN | H | — |
| 3-36 | OH | $CH_3(CH_2)_3$ | CN | H | — |
| 3-37 | $NH_2$ | H | OH | CN | — |
| 3-38 | $NH_2$ | $CH_3$ | OH | CN | — |
| 3-39 | $NH_2$ | $CH_3CH_2$ | OH | CN | — |
| 3-40 | $NH_2$ | $CH_3(CH_2)_2$ | OH | CN | — |
| 3-41 | $NH_2$ | $(CH_3)_2CH$ | OH | CN | — |
| 3-42 | $NH_2$ | $CH_3(CH_2)_3$ | OH | CN | — |
| 3-43 | OH | H | OH | CN | — |
| 3-44 | OH | $CH_3$ | OH | CN | — |
| 3-45 | OH | $CH_3CH_2$ | OH | CN | — |
| 3-46 | OH | $CH_3(CH_2)_2$ | OH | CN | — |
| 3-47 | OH | $(CH_3)_2CH$ | OH | CN | — |
| 3-48 | OH | $CH_3(CH_2)_3$ | OH | CN | — |
| 3-49 | NHAc | H | H | CN | — |
| 3-50 | NHAc | $CH_3$ | H | CN | — |
| 3-51 | NHAc | $CH_3CH_2$ | H | CN | — |
| 3-52 | NHAc | $CH_3(CH_2)_2$ | H | CN | — |
| 3-53 | NHAc | $(CH_3)_2CH$ | H | CN | — |
| 3-54 | NHAc | $CH_3(CH_2)_3$ | H | CN | — |
| 3-55 | NHAc | H | CN | OH | — |
| 3-56 | NHAc | $CH_3$ | CN | OH | — |
| 3-57 | NHAc | $CH_3CH_2$ | CN | OH | — |
| 3-58 | NHAc | $CH_3(CH_2)_2$ | CN | OH | — |
| 3-59 | NHAc | $(CH_3)_2CH$ | CN | OH | — |
| 3-60 | NHAc | $CH_3(CH_2)_3$ | CN | OH | — |
| 3-61 | NHAc | H | CN | H | — |
| 3-62 | NHAc | $CH_3$ | CN | H | — |
| 3-63 | NHAc | $CH_3CH_2$ | CN | H | — |
| 3-64 | NHAc | $CH_3(CH_2)_2$ | CN | H | — |
| 3-65 | NHAc | $(CH_3)_2CH$ | CN | H | — |
| 3-66 | NHAc | $CH_3(CH_2)_3$ | CN | H | — |
| 3-67 | NHAc | H | OH | CN | — |
| 3-68 | NHAc | $CH_3$ | OH | CN | — |
| 3-69 | NHAc | $CH_3CH_2$ | OH | CN | — |
| 3-70 | NHAc | $CH_3(CH_2)_2$ | OH | CN | — |
| 3-71 | NHAc | $(CH_3)_2CH$ | OH | CN | — |
| 3-72 | NHAc | $CH_3(CH_2)_3$ | OH | CN | — |
| 3-73 | NHBz | H | H | CN | — |
| 3-74 | NHBz | $CH_3$ | H | CN | — |
| 3-75 | NHBz | $CH_3CH_2$ | H | CN | — |
| 3-76 | NHBz | $CH_3(CH_2)_2$ | H | CN | — |
| 3-77 | NHBz | $(CH_3)_2CH$ | H | CN | — |
| 3-78 | NHBz | $CH_3(CH_2)_3$ | H | CN | — |
| 3-79 | NHBz | H | CN | OH | — |
| 3-80 | NHBz | $CH_3$ | CN | OH | — |
| 3-81 | NHBz | $CH_3CH_2$ | CN | OH | — |
| 3-82 | NHBz | $CH_3(CH_2)_2$ | CN | OH | — |
| 3-83 | NHBz | $(CH_3)_2CH$ | CN | OH | — |
| 3-84 | NHBz | $CH_3(CH_2)_3$ | CN | OH | — |
| 3-85 | NHBz | H | CN | H | — |
| 3-86 | NHBz | $CH_3$ | CN | H | — |
| 3-87 | NHBz | $CH_3CH_2$ | CN | H | — |
| 3-88 | NHAc | $CH_3(CH_2)_2$ | CN | H | — |
| 3-89 | NHBz | $(CH_3)_2CH$ | CN | H | — |
| 3-90 | NHBz | $CH_3(CH_2)_3$ | CN | H | — |
| 3-91 | NHBz | H | OH | CN | — |
| 3-92 | NHBz | $CH_3$ | OH | CN | — |
| 3-93 | NHBz | $CH_3CH_2$ | OH | CN | — |
| 3-94 | NHBz | $CH_3(CH_2)_2$ | OH | CN | — |
| 3-95 | NHBz | $(CH_3)_2CH$ | OH | CN | — |
| 3-96 | NHBz | $CH_3(CH_2)_3$ | OH | CN | — |

Among the above exemplary compounds, preferred are:

1-1, 1-2, 1-7, 1-8, 1-13, 1-14, 1-19, 1-20, 1-25, 1-26, 1-31, 1-32, 1-37, 1-38, 1-43, 1-44, 1-49, 1-50, 1-55, 1-56, 1-61, 1-62, 1-67, 1-68, 1-73, 1-77, 1-82, 1-83, 1-88, 1-89, 1-92, 1-97, 1-98, 1-103, 1-104, 2-1, 2- 2, 2- 7, 2- 8, 2-13, 2-14, 2-19, 2-20, 2-25, 2-26, 2-31, 2-32, 2-37, 2-38, 3-1, 3-2, 3-7, 3-8, 3-13, 3-14, 3-19, 3-20, 3-25, 3-26, 3-31, 3-32, 3-37, 3-38, 3-43, 3-44, 3-49, 3-50, 3-55, 3-56, 3-61, 3-62, 3-67, 3-68, 3-73, 3-74, 3-79, 3-80, 3-85, 3-86, 3-91 and 3-92.

Among the above exemplary compounds, more preferred are:

1-1, 1-2, 1-7, 1-8, 1-13, 1-14, 1-19, 1-20, 1-25, 1-26, 1-31, 1-32, 1-37, 1-38, 1-43, 1-44, 1-49, 1-50, 1-55, 1-56, 1-61, 1-62, 1-67, 1-68, 1-73, 1-77, 1-82, 1-83, 1-88, 1-89, 1-92, 1-97, 1-98, 1-103, 1-104, 2-1, 2-2, 2-7, 2-8, 2-13, 2-14, 2-19, 2-20, 2-25, 2-26, 2-31, 2-32, 2-37 and 2-38.

Among the above exemplary compounds, still more referred are:

1-1, 1-2, 1-7, 1-8, 1-13, 1-14, 1-19, 1-20, 1-25, 1-26, 1-31, 1-32, 1-37, 1-38, 1-43, 1-44, 1-49, 1-50, 1-55, 1-56, 1-61, 1-62, 1-67, 1-68, 2-1, 2-2, 2-7, 2- 8, 2-13 and 2-14.

Among the above exemplary compounds, most preferred are:

1-1, 1- 7, 1-13, 1-14, 1-19, 1-25, 1-31, 1-32, 1-37, 1-43, 1-49, 1-50, 1-55, 1-61, 1-67, 1-68, 2-1, 2- 7, 2-13 and 2-14.

Scheme 1

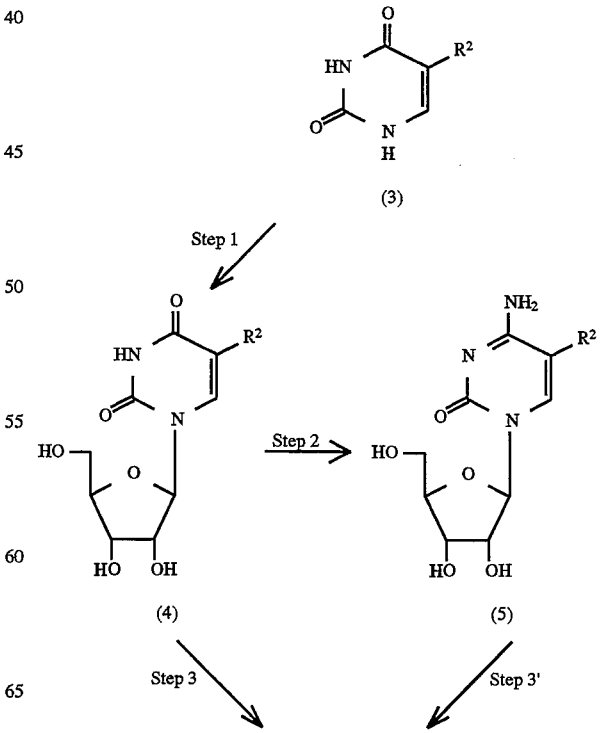

Scheme 1
-continued
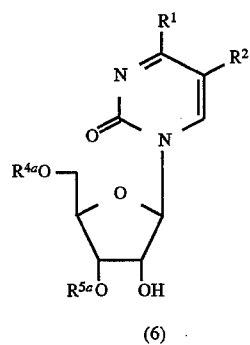
(6)
Scheme 2
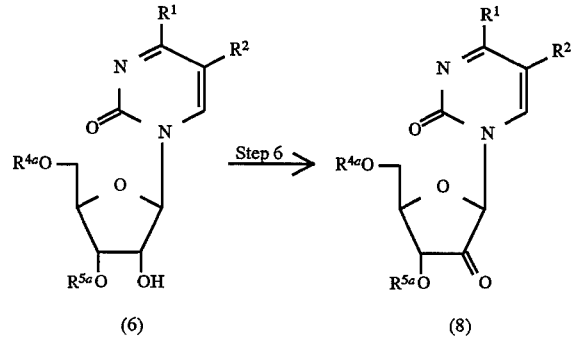
Scheme 3
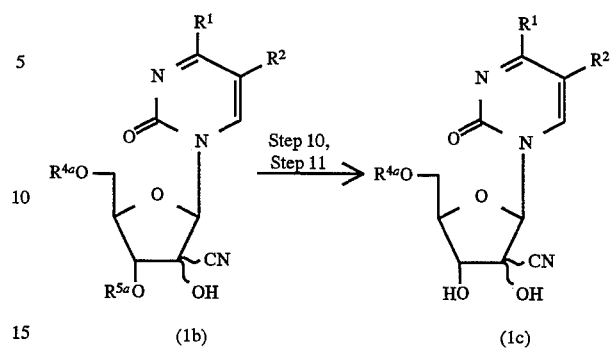
Scheme 4
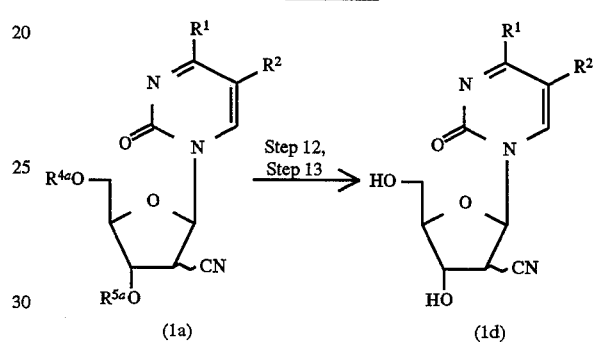
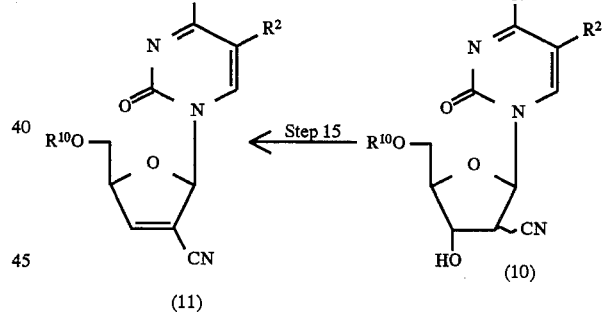
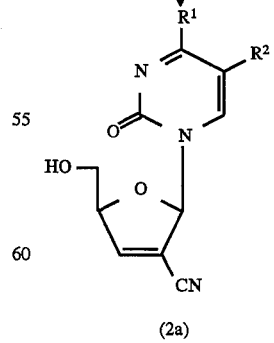
(2a)
Compounds (1) and (2) of the present invention can be prepared using uracil or a 5-lower alkyluracil, a known compound (3), [M. Muraoka, A. Tanaka and T. Ueda, Chem.
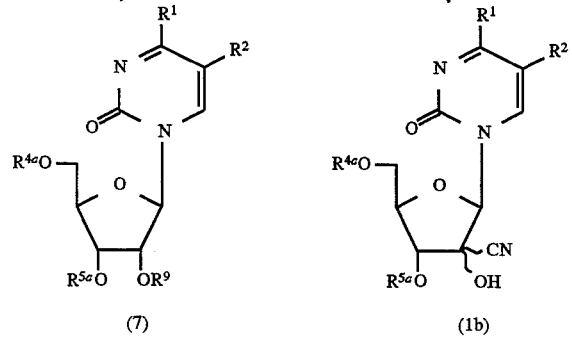
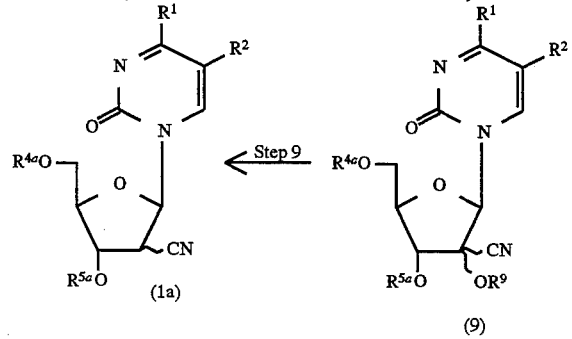

Pharm. Bull., 18, 261 (1970)] following the reaction steps shown in Reaction Schemes 1, 2, 3 and 4. In Schemes 1, 2, 3 and 4, $R^1$ and $R^2$ have the same meanings as defined above, $R^{4a}$ and $R^{5a}$ together represent a group of the formula: —$R^6R^7Si$—O—$SiR^{6'}R^{7'}$—(wherein $R^6$, $R^7$, $R^{6'}$ and $R^{7'}$ have the same meanings as defined above). $R^9$ represents an alkoxythiocarbonyl group having a $C_1$-$C_4$ alkyl or an aryloxythiocarbonyl group having a $C_6$-$C_{10}$ aryl. The alkyl having 1 to 4 carbon atoms includes methyl, ethyl propyl, butyl, etc., and the aryl having 6 to 10 carbon atoms includes phenyl, naphthyl, etc., preferably methyl and phenyl, respectively. $R^{10}$ represents a triarylmethyl group wherein the aryl moiety may be substituted, whereas the aryl moiety includes phenyl, naphthyl, etc., preferably phenyl. The substituent for the aryl moiety includes an alkyl group having 1 to 4 carbon atoms such as methyl, ethyl, propyl and butyl, an alkoxy group having 1 to 4 carbon atoms such as methoxy, ethoxy, propoxy and butoxy, and an acyloxy group having 2 to 4 carbon atoms such as acetoxy, propyloxy and butyryloxy, preferably methyl and methoxy group. X represents a halogen atom, preferably chlorine or bromine. The respective reaction steps will be explained below in detail.

Step 1

This step is for preparing Compound (4) by ribosylating Compound (3).

Ribosylation is generally carried out by methods customarily employed in the art, for example, as follows: (i) A mercury salt of compound (3) to be obtained by addition of an alcoholic solution of mercuric chloride to an aqueous sodium hydroxide solution of compound (3) is reacted with a known compound 2',3',5'-tri-O-benzoyl-D-ribosyl chloride in benzene. Sodium methoxide is allowed to act on the resulting compound in methanol to obtain Compound (4) [M. Muraoka, A. Tanaka and T. Ueda, Chem. Pharm. Bull., 18, 261 (1970)] and (ii) Compound (3) is reacted with trimethylsilyl chloride in benzene in the presence of an organic amine such as triethylamine to obtain bis(trimethylsilyl)uracil, which is reacted with 2',3',5'-tri-O-benzoyl-D-ribosyl chloride, followed by reaction of the resulting compound with sodium methoxide in methanol to obtain Compound (4) [T. Nishimura, B. Shimizu and I. Iwai, Chem. Pharm. Bull., 11, 1470 (1963)].

Step 2

This step is for preparing Compound (5) by converting the carbonyl moiety at the 4-position of Compound (4) to an amino group.

The conversion to an amino group is generally carried out by methods customarily employed in the art, for example, as follows:

(i) Hexamethyldisilazane and ammonium sulfate are allowed to act on Compound (4) with heating in anhydrous formamide to obtain Compound (5) [Compiled by Townsend and Tipson, Nucleic Acid Chemistry, 227 (1978)]

(ii) The hydroxyl groups at the 2'-, 3'- and 5'-positions of Compound (4) are protected by acetylation or benzoylation. In chloroform containing no alcohol, thionyl chloride and anhydrous dimethylformamide are acted on the resulting compound, followed by treatment with a methanol solution of ammonia to obtain Compound (5) [Compiled by Townsend and Tipson, Nucleic Acid. Chemistry, 223 (1978)]

(iii) The hydroxyl groups at the 2'-, 3'- and 5'-positions of Compound (4) are protected by acetylation or benzoylation, and diphosphorus pentasulfide is acted thereon in pyridine to obtain a 4-thio compound. A lower alkyl iodide such as methyl iodide and ethyl iodide and an alkali metal hydroxide such as sodium hydroxide is acted on the resulting compound to obtain a 4-alkylthio compound as an intermediate compound. The 4-alkylthio compound is further treated with a liquid ammonia to obtain Compound (5) [J. J. Fox, N. Miller and I. Wenpen, Journal of Medicinal Chemistry, 9, 101 (1966)].

Step 3

In this step, X—$R^6R^7Si$—O—$SiR^6R^7$—X is acted on the 3'- and 5'-positions of Compound (4) and these positions are protected at the same time to obtain Compound (5). This step is carried out by the known method [M. J. Robins, J. S. Wilson, L. Sawyer and M. N. G. James, Can. J. Chem., 61, 1911, (1983)].

As the solvent employable, there may preferably be mentioned a basic solvent such as pyridine.

Reaction is carried out at a temperature of −10° to 100° C., preferably 0° to 50° C.

While the reaction time varies depending on the compound and reaction temperature employed, it is usually from 1 hour to 30 hours, preferably 1 hour to 5 hours.

After completion of the reaction, for example, the solvent is distilled off, and the reaction mixture is poured in water. The resulting mixture is extracted with a water-immiscible solvent such as benzene, ether and ethyl acetate and the solvent is distilled off from the extract to obtain a compound. The thus obtained compound is used as such in the subsequent step. If desired, the compound can be purified by isolation by means of various chromatographic procedures or recrystallization.

Step 3'

This step is for acylating the amino group at the 4-position of Compound (5) and for acting X—$R^6R^7Si$—O—$SiR^6R^7$—X on the thus acylated compound to protect the 3'- and 5'-positions at the same time whereby to obtain Compound (6). The 3'- and 5'-positions can be protected in the same manner as in Step 3.

The acylation of the amino group at the 4-position is carried out by the method generally employed in the art. For example, in the case of an aliphatic acyl or aromatic acyl, the reactive derivative of the corresponding carboxylic acid such as an acid halide or an acid anhydride is allowed to react or the corresponding carboxylic acid is allowed to react in the presence of a condensing agent: or in the case of alkoxycarbonyl, alkenyloxycarbonyl or aralkyloxycarbonyl, a halogenoformic acid ester having the corresponding alkoxy, alkenyloxy or aralkyloxy group, or dialkyl dicarbonate, dialkenyl dicarbonate or diaralkyl dicarbonate having the corresponding alkyl, alkenyl or aralkyl group is allowed to react.

As the acid halide employable, there may be mentioned, for example, acid chlorides and acid bromides.

As the condensing agent employable, there may be mentioned, for example, N,N'-dicyclohexylcarbodiimide (DCC), 1,1'-oxalyldiimiazole, 2,2'-dipyridyldisulfide, N,N'-disuccinimidyl carbonate, N,N'-bis(2-oxo-3-oxazolydinyl)-phosphinic chloride, N,N'-carbodiimidazole, N,N'-disuccinimidyl oxalate (DSO), N,N'-diphthalimide oxalate (DPO), N,N'-bis(norbornenylsuccinimidyl)oxalate (BNO), 1,1'-bis(benzotriazolyl) oxalate (BBTO), 1,1'-bis(6-chlorobenzotriazolyl) oxalate (BCTO), 1,1'-bis(6-trifluoromethylbenzotriazolyl)oxalate (BTBO), etc.

The solvent employable is not particularly limited unless it inhibits the reaction and includes aromatic hydrocarbons such as benzene, toluene and xylene, ethers such as diethyl ether, diisopropyl ether, tetrahydrofuran, dioxane, dimethoxyethane and diethylene glycol diemethyl ether, alcohols such as methanol, ethanol, n-propanol, isopropanol, n-butanol, isobutanol, t-butanol, isoamyl alcohol, diethylene glycol, glycerol, octanol, cyclohexanol and methyl cellosolve, ketones such as acetone, methyl ethyl ketone, methyl isobutyl ketone, isophorone and cyclohexanone, nitriles such as acetonitrile and isobutyronitrile, amides such as formamide, dimethylformamide, dimethylacetamide and hexamethylphosphorotriamide, sulfoxides such as dimethyl sulfoxide and sulfolane, and mixed solvents of these organic solvents and water, preferably aromatic hydrocarbons such as benzene, toluene and xylene, ethers such as diethyl ether, diisopropyl ether, tetrahydrofuran, dioxane, dimethoxyethane and diethylene glycol dimethyl ether, alcohols such as-methanol, ethanol, n-propanol, isopropanol, n-butanol, isobutanol, t-butanol, isoamyl alcohol, diethylene glycol, glycerol, octanol, cyclohexanol and methyl cellosolve, ketones such as acetone, methyl ethyl ketone, methyl isobutyl ketone, isophorone and cyclohexanone, nitriles such as acetonitrile and isobutyronitrile, amides such as formamide, dimethylformamide, dimethylacetamide and hexamethylphosphorotriamide, sulfoxides such as dimethyl sulfoxide and sulfolane, and mixed solvents of these organic solvents and water.

Reaction is carried out at a temperature of 0° C. to 150° C., preferably 0° C. to 100° C.

While reaction time varies depending on the compound, reaction temperature, etc. employed, it is usually from 1 hour to 30 hours, preferably 2 hours to 5 hours.

After completion of the rection, for example, the solvent is distilled off, and the reaction mixture is poured in water. The resulting mixture is extracted with a water-immiscible solvent such as benzene, ether and ethyl acetate and the solvent is distilled off from the extract to obtain a compound. The thus obtained compound is usually used as such in the subsequent step. If desired, the compound can be purified by isolation by means of various chromatographic procedures or recrystallization.

Step 4

This step is for preparing Compound (7) by treating Compound (6) with a thiocarbonylating reagent in an inert solvent to effect thiocarbonylation by substitution of the hydroxyl group at the 2'-position of Compound (5).

The solvent employable is not particularly limited unless it inhibits the reaction and includes amides such as dimethylformamide and dimethylacetamide, sulfoxides such as dimethyl sulfoxide and nitriles such as acetonitrile, preferably acetonitrile.

While the reagent employable is not particularly limited, if it is a hydroxyl group thiocarbonylating reagent, and it includes lower alkoxycarbonyl halides such as methoxythiocarbonyl chloride and ethoxythiocarbonyl chloride, and arylthiocarbonyl halides such as phenoxythiocarbonyl chloride and naphthoxythiocarbonyl chloride.

Reaction is carried out at a temperature of −20° C. to 50° C., preferably −10° C. to 10° C.

While reaction time varies depending on the compound, reaction temperature, etc. employed, it is usually from 1 hour to 30 hours, preferably 2 hours to 5 hours.

In order to carry out efficiently the reaction, organic amines such as 4,4-dimethylaminopyridine and triethylamine can be used.

After completion of the reaction, the desired compound can be obtained by the conventional method. For example, the reaction mixture is poured in water, the resulting mixture is extracted with a water-immiscible solvent such as benzene, ether and ethyl acetate and the solvent is distilled off from the extract to obtain the desired compound. The thus obtained compound is usually used as such in the subsequent step. If desired, the compound can be purified by isolation by means of various chromatographic procedures or recrystallization.

Step 5

This step is for preparing Compound (1a), which is the desired compound (1) wherein $R^4$ and $R^5$ together represent a group of the formula: —$R^6R^7Si$—O—$SiR^6R^7$—; and $R^3$ represents a hydrogen atom by treating Compound (7) obtained in Step 4 with a reducing agent and a nitrilizing reagent in an inert solvent.

The solvent employable is not particularly limited unless it inhibits the reaction and includes aliphatic hydrocarbons such as hexane, heptane, ligroin and petroleum ether, aromatic hydrocarbons such as benzene, toluene and xylene, ethers such as diethyl ether, diisopropyl ether, tetrahydrofuran, dioxane, dimethoxyethane and diethylene glycol diemethyl ether and aromatic hydrocarbons such as benzene, toluene and xylene, preferably aromatic hydrocarbons such as benzene and toluene.

The nitrilizing regent employable preferably includes alkylisonitriles such as t-butylisonitrile, while the reducing reagent employable preferably includes trialkyltin hydride having 1 to 4 carbon atoms such as tributyltin hydride.

Reaction is carried out at a temperature of 50° C. to 250° C., preferably 80° C. to 150° C. While reaction time varies depending on the compound, reaction temperature, etc. employed, it is usually from 30 minutes to 12 hours, preferably 1 hour to 5 hours.

In order to carry out efficiently the reaction, a radical initiator such as azoisobutyronitrile can be used as a catalyst.

The Compound (1a) obtained immediately after the reaction in this step is a mixture of compounds wherein the coordination of the nitrile group is α- and β-coordination, respectively. Such compounds can be subjected, for example, to adsorption or ion exchange chromatography using various carriers such as an activated carbon and silica gel, gel filtration using a Cephadex column, or recrystallization using an organic solvent such as ether, ethyl acetate and chloroform to separate the mixture into the respective compounds depending on the purpose.

Step 6

This step is for preparing Compound (8) by oxidizing the hydroxyl group at the 2'-position of Compound (6) and can be carried out using known methods. [F. Hansske et al., Tetrahedron 40, 125, (1984)].

The solvent employable is not particularly limited as long as it does not inhibit the reaction and can dissolve the starting materials therein to some degree, and it includes aromatic hydrocarbons such as benzene, toluene and xylene, halogenated hydrocarbons such as methylene chloride and chloroform, ethers such as ether, tetrahydrofuran, dioxane and dimethoxyethane, amides such as diemethylformamide, dimethylacetamide and hexamethylphosphorotriamide, sulfoxides such as dimethyl sulfoxide, ketones such as acetone and methyl ethyl ketone, and nitriles such as acetonitrile, preferably halogenated hydrocarbons such as methylene chloride and chloroform.

Reaction is carried out at a temperature of 0° C. to 100° C., preferably 10° C. to 40° C.

While reaction time varies depending on the compound, reaction temperature, etc. employed, it is usually from 10 minutes to 12 hours, preferably 30 minutes to 3 hours.

Incidentally, the above oxidation reaction can be accelerated by adding an interlayer moving catalyst such as triethylbenzylammonium chloride and tributylbenzylammonium bromide.

Reaction is carried out at a temperature of 0° C. to 100° C., preferably 10° C. to 40° C.

While reaction time varies depending on the compound, reaction temperature, etc. employed, it is usually 10 minutes to 12 hours, preferably 30 minutes to 3 hours.

Compound (8) obtained in this step can be collected, separated and purified by combining suitably various methods. For example, the reaction mixture is poured in water, the resulting mixture is extracted with a water-immiscible solvent such as benzene, ether and ethyl acetate, and the solvent is distilled off from the extract to obtain the Compound (8). If necessary, thus obtained compound can further be subjected, for example, to adsorption or ion exchange chromatography using various carriers such as an activated carbon and silica gel, gel filtration using a Cephadex column or recrystallization using an organic solvent such as ether, ethyl acetate and chloroform.

Step 7

This step is for preparing the desired Compound (1b) by acting a cyanide on Compound (8) in an inert solvent in the presence of a base.

The solvent employable is not particularly limited unless it inhibits the reaction and includes a mixed solvent of an aliphatic hydrocarbon such as hexane, heptane, ligroin and petroleum ether with water, a mixed solvent of an aromatic hydrocarbon such as benzene, toluene and xylene with water, a mixed solvent of an ether such as diethyl ether, diisopropyl ether, tetrahydrofuran, dioxane, dimethoxyethane and diethylene glycol diemethyl ether with water, preferably a mixed solvent of an ether with water.

The base employable is not particularly limited, and there may be mentioned organic bases and inorganic bases including alkali methal hydroxides such as sodium hydroxide and potassium hydroxide and alkali metal carbonates such as sodium carbonate and potassium carbonate, preferably alkali metal hydrogencarbonate.

The cyanide employable is not particularly limited as long as it is soluble in water to form a cyano ion, and preferably includes cyanides of alkali metals such as sodium cyanide and potassium cyanide.

Reaction is carried out at a temperature of 0° C. to 100° C., preferably 10° C. to 40° C.

While reaction time varies depending on the compound, reaction temperature, etc. employed, it is usually 30 minutes to 96 hours, preferably 5 hours to 24 hours.

Compound (1b) obtained in this step can be collected, separated and purified by combining suitably various methods. For example, the reaction mixture is poured in water, the resulting mixture is extracted with a water-immiscible solvent such as benzene, ether and ethyl acetate, and the solvent is distilled off from the extract to obtain the desired compound. If necessary, thus obtained compound can further be subjected, for example, to adsorption or ion exchange chromatography using various carriers such as an activated carbon and silica gel, gel filtration using a Cephadex column or recrystallization using an organic solvent such as ether, ethyl acetate and chloroform.

The compound (1b) obtained immediately after the reaction in this step is a mixture of compounds wherein the coordination of the nitrile group is α- and β-configuration, respectively. Such compounds can be subjected, for example, to adsorption or ion exchange chromatography using various carriers such as an activated carbon and silica gel, gel filtration using a Cephadex column or recrystallization using an organic solvent such as ether, ethyl acetate and chloroform to separate the mixture into the respective compounds depending on the purpose.

Step 8

This step is for preparing Compound (9) by treating Compound (1b) with a thiocarbonylating reagent in an inert solvent to effect thiocarbonylation by substitution of the hydroxyl group at the 2'-position of Compound (1b) and can be carried out in the same manner as in Step 4.

Step 9

This step is for preparing Compound (1a) by reductively eliminating the thiocarbonyloxy group at the 2'-position of Compound (9).

The solvent employable is not particularly limited unless it inhibits the reaction and includes aliphatic hydrocarbons such as hexane, heptane, ligroin and petroleum ether, aromatic hydrocarbons such as benzene, toluene and xylene, ethers such as diethyl ether, diisopropyl ether, tetrahydrofuran, dioxane, dimethoxyethane and diethylene glycol dimethyl ether and aromatic hydrocarbons such as benzene and toluene, preferably aromatic hydrocarbons such as benzene and toluene.

The reagent employable includes preferably trialkyltin hydrides such as tributyltin hydride.

Reaction is carried out usually at a temperature of 50° C. to 250° C., preferably at the boiling point of the solvent employed.

Reaction time is usually from 30 minutes to 10 hours, preferably 30 minutes to 3 hours.

In order to carry out efficiently the reaction, a radical initiator such as azoisobutyronitrile can be used as a catalyst.

The desired compound thus obtained can be collected, separated and purified by combining suitably various methods. For example, the reaction mixture is poured into water, the resulting mixture is extracted with a water-immiscible solvent such as benzene, ether and ethyl acetate, and the solvent is distilled off from the extract to obtain the desired compound. If necessary, thus obtained compound can further be subjected, for example, to adsorption or ion exchange chromatography using various carriers such as an activated carbon and silica gel, gel filtration using a Cephadex column or recrystallization using an organic solvent such as ether, ethyl acetate and chloroform.

The compound (1a) obtained immediately after the reaction in this step is a mixture of compounds wherein the coordination of the nitrile group is α and β-configuration, respectively. Such compounds can be subjected, for example, to adsorption or ion exchange chromatography using various carriers such as an activated carbon and silica gel, gel filtration using a Cephadex column or recrystallization using an organic solvent such as ether, ethyl acetate and chloroform to separate the mixture into the respective compounds depending on the purpose.

Steps 10 and 12

These steps are for preparing the desired Compounds (1c) and (1d) by acting an eliminating agent for $R^{4a}$ and $R^{5a}$ on Compounds (1b) and (1a) in an inert solvent to remove the substituent on the amino group, as necessary.

While the solvent employable in the reaction of eliminating $R^{4a}$ and $R^{5a}$ is not particularly limited unless it inhibits the reaction, there may be mentioned preferably ethers such as tetrahydrofuran and dioxane. The reagent employable is not particularly limited as long as it is usually used for eliminating a silyl group, and there may be mentioned one which forms a fluorine anion such as tetrabutylammonium fluoride.

Reaction is carried out at a temperature of 0° C. to 40° C., preferably at room temperature.

While the reaction time varies depending on the reaction temperature, it is from 10 minutes to 24 hours, preferably 1 hour to 5 hours.

The desired compound thus obtained can be collected, separated and purified by combining suitably various methods. For example, the reaction mixture is poured into water, the resulting mixture is extracted with a water-immiscible solvent such as benzene, ether and ethyl acetate, and the solvent is distilled off from the extract to obtain the Compound (8). If necessary, thus obtained compound can further be subjected, for example, to adsorption or ion exchange chromatography using various carriers such as an activated carbon and silica gel, gel filtration using a Cephadex column or recrystallization using an organic solvent such as ether, ethyl acetate and chloroform.

Incidentally, in the case where $R^2$ is a substituted amino group, it can sometimes be eliminated simultaneously.

Steps 11 and 13

These steps are for preparing Compounds (1c) and (1d) of the present invention by acting an eliminating agent for the protective group to eliminate the substituent on $R^2$ in an inert solvent, and this step is selected if desired.

While the elimination of the protective moiety varies depending on the protective moiety, it is usually carried out by a method known in the art as follows:

a) In the case where the protective moiety is an aliphatic acyl, an aromatic acyl or an alkyloxycarbonyl; such protective moiety can be removed by treating with an acid in the presence or absence of a solvent. As the acid employable, there may be mentioned hydrochloric acid, acetic acid, sulfuric acid, phosphoric acid and hydrobromic acid, preferably acetic acid.

As the solvent employable, there may be mentioned alcohols such as methanol, ethanol, n-propanol, isopropanol, n-butanol, isobutanol, t-butanol, isoamyl alcohol, diethylene glycol, glycerol and octanol, aromatic hydrocarbons such as benzene, toluene and xylene, ethers such as tetrahydrofuran and dioxane, and a mixed solvent of such organic solvent and water.

Reaction is carried out at a temperature of 0° C. to 40° C., preferably at room temperature.

While the reaction time varies depending on the reaction temperature, it is from 10 minutes to 24 hours, preferably 1 hour to 5 hours.

The desired compound thus obtained can be collected, separated and purified by combining suitably various methods. Usually, the reaction mixture is distilled off and the residue is subjected, for example, to adsorption or ion exchange chromatography using various carriers such as an activated carbon and silica gel, gel filtration using a Cephadex column or recrystallization using an organic solvent such as ether, ethyl acetate and chloroform.

b) In the case where the protective moiety is an aralkyloxycarbonyl: such protective moiety can be eliminated by catalytical reduction using a catalyst.

As the solvent employable, there may be mentioned alcohols such as methanol, ethanol, n-propanol, isopropanol and n-butanol, saturated hydrocarbons such as hexane and cyclohexane, ethers such as tetrahydrofuran and dioxane, and lower fatty acids such as acetic acid and propionic acid, preferably methanol, ethanol, acetic acid and propionic acid.

As the catalyst employable, there may preferably be mentioned platinum and palladium on carbon.

Reaction is carried out at a temperature of 0° C. to 40° C., preferably at room temperature.

While the reaction time varies depending on the reaction temperature, it is from 10 minutes to 24 hours, preferably 1 hour to 5 hours.

The desired compound thus obtained can be collected, separated and purified by combining suitably various methods. Usually, the reaction mixture is distilled off and the residue is subjected, for example, to adsorption or ion exchange chromatography using various carriers such as an activated carbon and silica gel, gel filtration using a Cephadex column or recrystallization using an organic solvent such as ether, ethyl acetate and chloroform.

Step 14

This step is for preparing Compound (10) by acting a protecting reagent on Compound (1d) in an inert solvent.

As the solvent employable, there may be mentioned basic solvents such as pyridine and neutral solvents such as benzene, toluene and ether.

While the protecting reagent employable is not particularly limited as long as it can specifically protect only the hydroxyl group at the 5'-position, triphenylchloromethane, monomethoxytrityl chloride, dimethoxytrityl chloride, etc. can suitably be used.

Reaction is usually carried out at a temperature of 0° C. to 100° C., preferably −10° C. to 50° C.

The reaction time is usually from 30 minutes to 10 hours, preferably 1 hour to 5 hours.

When a neutral solvent is used as the solvent, an organic amine such as triethylamine can be used in order to carry out the reaction efficiently.

The compound thus obtained can be collected, separated and purified by combining suitably various methods. For example, the reaction mixture is poured into water, the resulting mixture is extracted with a water-immiscible solvent such as benzene, ether and ethyl acetate, and the solvent is distilled off from the extract to obtain the desired compound. If necessary, thus obtained compound can be subjected, for example, to adsorption or ion exchange chromatography using various carriers such as an activated carbon and silica gel, gel filtration using a Cephadex column or recrystallization using an organic solvent such as ether, ethyl acetate and chloroform.

Step 15

This step is for preparing Compound (11) by acting a hydroxyl group eliminating agent on Compound (10) in an inert solvent.

As the solvent employable, there may be mentioned, for example, aliphatic hydrocarbons such as hexane, heptane, ligroin and petroleum ether, aromatic hydrocarbons such as benzene, toluene and xylene, ethers such as diethyl ether, diisopropyl ether, tetrahydrofuran, dioxane, dimethoxyethane and diethylene glycol dimethyl ether, ketones such as acetone, methyl ethyl ketone, methyl isobutyl ketone, isophorone and cyclohexanone, nitro compounds such as nitroethane and nitrobenzene, nitriles such as acetonitrile and isobutyronitrile, amides such as formamide, dimethylformamide, dimethylacetamide and hexamethyl phophorotriamide and sulfoxides such as dimethyl sulfoxide and sulfolane, preferably aromatic hydrocarbons such as benzene, toluene and xylene.

As the reagent employable, there may be mentioned compounds having a thiocarbonyl group such as thiocarbonyl diimidazole and phenoxythiocarbonyl chloride.

Reaction is carried out at a temperature of −10° C. to 50° C., preferably at room temperature.

The reaction time is usually from 1 hour to 24 hours, preferably 3 hours to 10 hours.

The desired compound thus obtained can be collected, separated and purified by combining suitably various methods. For example, the reaction mixture is poured into water, the resulting mixture is extracted with a water-immiscible solvent such as benzene, ether and ethyl acetate, and the solvent is distilled off from the extract to obtain the desired compound. If necessary, thus obtained compound can be subjected, for example, to adsorption or ion exchange chromatography using various carriers such as an activated carbon and silica gel, gel filtration using a Cephadex column or recrystallization using an organic solvent such as ether, ethyl acetate and chloroform.

Step 16

This step is for preparing the desired Compound (2a) of the present invention by acting a hydroxyl group deprotecting agent on Compound (11) in an inert solvent.

While the elimination of the protecting moiety varies depending on the protecting moiety, it is usually carried out by a method known in the art, and in the case where the protecting moiety is a triarylmethyl which is a preferable protective group, it is carried out as follows:

While the solvent employable is not particularly limited unless it participates in this reaction, it preferably includes alcohols such as methanol and ethanol, ethers such as tetrahydrofuran and dioxane, and mixed solvent with such organic solvent with water.

The reagent to be used is usually an acid. The acid is not particularly limited as long as it is used as a Bronsted acid, and preferably includes an inorganic acid such as hydrochloric acid and sulfuric acid, and an organic acid such as acetic acid and p-toluenesulfonic acid. In addition, a strong acidic cation exchange resin such as Dowex 50W can be used.

Reaction is usually carried out at a temperature of 0° C. to 50° C., preferably at room temperature.

While the reaction time varies depending on the starting materials, types of acids, etc., it is usually from 10 minutes to 18 hours, preferably 30 minutes to 5 hours.

The desired compound thus obtained can be collected, separated and purified by combining suitably various methods. For example, the reaction mixture is poured into ater, the resulting mixture is extracted with a water-immiscible solvent such as benzene, ether and ethyl acetate, and the solvent is distilled off from the extract to obtain the desired compound. If necessary, thus obtained compound can be subjected, for example, to adsorption or ion exchange chromatography using various carriers such as an activated carbon and silica gel, gel filtration using a Cephadex column or recrystallization using an organic solvent such as ether, ethyl acetate and chloroform.

BEST MODE FOR PRACTICING THE INVENTION

The present invention is described further in detail by way of Examples, Reference Examples and Preparation Examples. In Examples, TIPDS stands for (1,1,3,3-tetraisopropyldisilox-1,3-diyl).

EXAMPLE 1

1-[2'-Cyano-3', 5'-O-(1,1,3,3-tetraisopropyldisilox-1,3-diyl)-β-D-ribofuranosyl]thymine In 15 ml of ether-water (2:1) was dissolved 997 mg of 1-(3,5-O-TIPDS-β-D-erythro-pentofuran-2-urosyl)thymine, and to the resulting solution were added 196 mg of sodium cyanide and 336 mg of sodium hydrogencarbonate, followed by stirring at room temperature for 36 hours. After completion of the reaction, to the reaction mixture was added ethyl acetate, and the mixture was washed three times with water. The ethyl acetate layer was dried over anhydrous sodium sulfate and the solvent was removed by evaporation. The residue was purified over column chromatography using a silica gel column (φ2.4×9.5 cm) (eluted with hexane/ethyl acetate (2:1)) to obtain 1.03 g (97.5%) Of the title compound as a white foam. $^1$H-NMR(CDCl$_3$) δppm:

9.20 and 8.52(1H, bs) 7.43 and 7.36(1H, d, J=6.8 Hz) 6.22 and 6.00(1H, s) 5.08(1H, bs) 4.32-3.94(4H, m) 1.92 (3H, d, J=1.7 Hz) 1.12-1.07(28H, m)

EXAMPLE 2

1-(2'-Cyano-2'-deoxy-3',5'-O-TIPDS-β-D-arabinofuranosyl)-thymine

In 2 ml of anhydrous acetonitrile were dissolved 100 mg of the compound of Example 1 and 10 mg of 4,4-dimethylaminopyridine (hereinafter abbreviated as DMAP), and to the resulting solution were added 39 µl of phenoxycarbonyl chloride and 40 µl of triethylamine at 0° C. in an argon gas stream, followed by stirring for 3 hours. After completion of the reaction, ethyl acetate was added to the reaction mixture and the mixture was washed three times with water. The mixture was dried over anhydrous sodium sulfate, and the solvent was removed by evaporation. The residue was purified over column chromatography using a silica gel column (φ1.6×10 cm) (eluted with methanol/chloroform (1:99)) to obtain 71 mg (73.3%) of the title compound as a yellowish white foam. $^1$H-NMR(CDCl$_3$) δppm:

7.36(1H, d, J=1.2 Hz) 6.28(1H, d, J=7.3 Hz) 4.67(1H, dd, J=8.3, 9.3 Hz) 4.17(1H, dd, J=2.2, 13.2 Hz) 4.04(1H, dd, J=2.9, 13.2 Hz) 3.78(1H, ddd, J=2.2, 2.9, 8.3 Hz) 3.58(1H, dd, J=7.3, 9.3 Hz) 1.94(1H, d, J=1.2 Hz) 1.15-1.04(28H, m)

EXAMPLE 3

1-(2'-Cyano-2'-deoxy-β-D-arabinofuranosyl)thymine

In 3 ml of anhydrous tetrahydrofuran (THF) was dissolved 178 mg of the compound of Example 2, and to the resulting solution were dropwise added 20 µl of acetic acid and 0.70 ml of a solution of tetrabutylammonium fluoride in 1M-THF at 0° C. in an argon gas stream, followed by stirring for 1.5 hours. After completion of the reaction, the reaction mixture was concentrated, purified over column chromatography using a silica gel column (φ1.8×8 cm) (elated with ethanol/chloroform (8-10: 92-90)) and crystallized from ether and ethanol to obtain 27 mg of the title compound as white crystals. $^1$H-NMR(CDCl$_3$) δppm:

11.49(1H, s) 7.85(1H, d, J=1.1 Hz) 6.25(1H, d, J=6.0 Hz) 6.20(1H, d, J=7.1 Hz) 5.30(1H, t, J=4.9 Hz) 4.47(1H, ddd, J=6.0, 8.2, 8.8 Hz) 3.89(1H, dd, J=7.1, 8.8 Hz) 3.74(1H, ddd, J=2.2, 3.3, 8.2 Hz) 3.62(1H, ddd, J=3.3, 4.9, 11.1 Hz) 1.78(3H, d, J=1.1 Hz)

EXAMPLE 4

1-(2'-Cyano-2'-deoxy-3',5'-O-TIPDS-β-D-arabinofuranosyl)-N$^4$-benzoylcytosine

The procedures in Example 1 were analogously repeated using 294 mg of N$^4$-benzoyl-1-(3,5-O-TIPDS-β-D-erythro-pentofuran-2-urosyl)cytosine. Further, the procedures in Example 2 were analogously repeated using the resulting crude product to obtain 174 mg (49.1%) of the title compound as a yellowish white solid. $^1$H-NMR(CDCl$_3$) δppm:

8.89(1H, bs) 8.11(1H, d, J=7.7 Hz) 7.93-7.45(5H, m) 7.67(1H, d, J=7.7 Hz) 6.36(1H, d, J=6.6 Hz) 4.67(1H, t, J=8.1 Hz) 4.18(1H, dd, J=2.9, 13.2 Hz) 4.10(1H, dd, J=2.9, 13.2 Hz) 3.91(1H, ddd, J=2.9, 2.9, 8.1 Hz) 3.75(1H, dd, J=6.6, 8.1 Hz) 1.15-1.04(28H, m)

EXAMPLE 5

1-(2'-Cyano-2'-deoxy-β-D-arabinofuranosyl)-N$^4$-benzoylcytosine

The procedures in Example 3 were analogously repeated using 100 mg of the compound of Example 4 and crystallization from methanol was carried out to obtain 25 mg of the title compound as white crystals. $^1$H-NMR(DMSO-$d_6$) δppm:

11.34(1H, bs) 8.45(1H, d, J=7.7 Hz) 8.00(2H, m) 7.66-7.49(3H, m) 7.42(1H, d, J=7.7 Hz) 6.29(1H, d, J=5.5 Hz) 6.25(1H, d, J=7.1 Hz) 5.28(1H, bs) 4.47(1H, ddd, J=5.5, 7.1, 7.7 Hz) 3.94(1H, dd, J=7.1, 7.7 Hz) 3.86(1H, ddd, J=2.5, 3.8, 7.1 Hz) 3.79(1H, bd, J=12.5 Hz) 3.65(1H, bd, J=12.5 Hz)

EXAMPLE 6

1-(2'-Cyano-2'-deoxy-3',5'-O-TIPDS-β-D-arabinofuranosyl)-$N^4$-acetylcytosine

The procedures in Example 4 were analogously repeated using 2 g of $N^4$-acetyl-1-(3,5-O-TIPDS-β-D-erythro-pentofuran-2-urosyl)cytosine, and after purification, the crystals obtained by evaporation of the solvent were collected by filtration with ether-hexane to obtain 703 mg of the title compound as white crystals. $^1$H-NMR(CDCl$_3$) δppm:

9.92(1H, bs) 8.07(1H, d, J=7.7 Hz) 7.55(1H, d, J=7.7 Hz) 6.34(1H, d, J=7.0 Hz) 4.63(1H, t, J=8.8 Hz) 4.18(1H, dd, J=2.4, 13.4 Hz) 4.06(1H, dd, J=2.7, 13.4 Hz) 3.89(1H, ddd, J=2.4, 2.7, 8.8 Hz) 3.72(1H, dd, J=7.0, 8.8 Hz) 2.30(3H, s) 1.13-1.03(28H, m)

EXAMPLE 7

1-(2'-Cyano-2'-deoxy-β-D-arabinofuranosyl)-$N^4$-acetylcytosine

The procedures in Example 3 were analogously repeated using 1.07 g of the compound of Example 6, and after purification, the crystals obtained by evaporation of the solvent were collected by filtration with ether-hexane to obtain 480 mg of the title compound as white crystals. $^1$H-NMR(DMSO-$d_6$) δppm:

10.97(1H, bs) 8.36(1H, d, J=7.7 Hz) 7.26(1H, d, J=7.7 Hz) 6.27(1H, d, J=6.1 Hz) 6.22(1H, d, J=7.1 Hz) 5.24(1H, bs) 4.43(1H, ddd, J=6.1, 7.1, 7.1 Hz) 3.92(1H, t, J=7.1 Hz) 3.84(1H, ddd, J=2.8, 3.3, 7.1 Hz) 3.76(1H, bd, J=12.1 Hz) 3.63(1H, bd, J=12.1 Hz) 2.11(3H, s)

EXAMPLE 8

1-(2'-Cyano-2'-deoxy-β-D-arabinofuranosyl)cytosine

In 55 ml of methanol was dissolved 100 mg of the compound of Example 7, and to the resulting solution was added 2.5 ml of acetic acid, followed by refluxing with heating in an oil bath for 5 days. After completion of the reaction, the solvent was evaporated and the residue was purified over a silica gel column (φ1.8×7 cm) (eluted with methanol/chloroform (12-15:88-85)) and further over HPLC (D-ODS-5.5% methanol-water) and then crystallized from ethanol-ether to obtain 29 mg of the title compound as white crystals. $^1$H-NMR(DMSO-$d_6$) δppm:

7.83(1H, d, J=7.1 Hz) 7.27(2H, bs) 6.17(1H, d, J=6.6 Hz) 6.15(1H, d, J=7.1 Hz) 5.79(1H, d, J=7.6 Hz) 5.14(1H, t, J=4.9 Hz) 4.40(1H, ddd, J=6.6, 7.1, 7.7 Hz) 3.77(1H, t, J=7.1 Hz) 3.74(1H, ddd, J=2.8, 4.5, 7.7 Hz) 3.73(1H, ddd, J=2.8, 4.9, 12.6 Hz) 3.60(1H, ddd, J=2.8, 4.9, 12.6 Hz)

EXAMPLE 9

1-(2'-Cyano-2'-deoxy-β-D-arabinofuranosyl)cytosine monohydrochloride

In 5 ml of 3% hydrochloric acid-methanol was dissolved 40 mg of the compound of Example 8, followed by stirring at room temperature for 50 minutes. After completion of the reaction, crystallization was carried out using ethanol-ether to obtain 26 mg of the title compound as white crystals. $^1$H-NMR(DMSO-$d_6$) δppm:

9.80(1H, s) 8.75(1H, s) 8.30(1H, d, J=7.7 Hz) 6.21(1H, d, J=7.2 Hz) 6.12(1H, d, J=7.7 Hz) 4.43(1H, dd, J=7.1, 7.7 Hz) 3.97(1H, t, J=7.1 Hz) 3.83(1H, ddd, J=2.8, 3.3, 7.7 Hz) 3.76(1H, dd, J=2.8, 12.6 Hz) 3.62(1H, dd, J=3.8, 12.6 Hz)

EXAMPLE 10

1-(2'-Cyano-2'-deoxy-3',5'-O-TIPDS-β-D-ribofuranosyl)thymine

In 4 ml of anhydrous toluene was suspended 400 mg of 3',5'-O-TIPDS-2'-O-phenoxythiocarbonylthymidine, and to the resulting suspension was added 1.98 ml of t-butylisonitrile, followed by heating in an oil bath at 100° C. in an argon gas stream. To the resulting mixture was dropwise added 4 ml of a solution of azoisobutyronitrile (50 mg) and tributyltin hydride (0.25 ml) in toluene over an hour using a syringe pump. After three hours from the completion of the dropwise addition, 0.25 ml of tributyltin hydride was added to the mixture, and the mixture was stirred for 19 hours, followed by evaporation of the solvents. The residue was purified over column chromatography using a silica gel column (2.2×8 cm) (eluted with chloroform) to obtain 70 mg of the title compound as a yellow foam. $^1$H-NMR(CDCl$_3$) δppm:

8.57(1H, bs) 7.38(1H, d, J=1.1 Hz) 6.01(1H, d, J=2.6 Hz) 4.22-4.01(4H, m) 3.48(1H, dd, J=2.6, 4.8 Hz) 1.90(3H, d, J=1.1 Hz) 1.10-1.01(28H, m)

EXAMPLE 11

1-(2'-Cyano-2'-deoxy-β-D-ribofuranosyl)thymine

The procedures in Example 3 were analogously repeated using 70 mg of the compound of Example 10, and after purification, the solid obtained by evaporating the solvent was collected by filtration with ether to obtain 17 mg of the title compound as a yellowish white solid. $^1$H-NMR (DMSO-$d_6$) δppm:

11.49(1H, bs) 7.64(1H, d, J=1.1 Hz) 6.32(1H, d, J=5.5 Hz) 6.27(1H, d, J=8.2 Hz) 5.22(1H, bs) 4.37(1H, ddd, J=2.8, 5.5, 5.5 Hz) 3.93(1H, m) 3.75(1H, dd, J=5.5, 8.2 Hz) 3.66-3.51(2H, m) 1.78(3H, d, J=1.1 Hz)

EXAMPLE 12

1-(2'-Cyano-2',3'-deoxy-2',3'-didehydro-β-D-ribofuranosyl)thymine

In 3 ml of acetic acid was dissolved 112 mg of the compound of Reference example 3 and the resulting solution was stirred at room temperature for 1 hour. After completion of the reaction, the solvent was evaporated and the residue was purified over a silica gel column (φ1.6×8.5 cm) (eluted with ethanol/chloroform=8:92). The solvent was evaporated and the crystals precipitated were collected by filtration using ether-hexane to obtain 22 mg of the title compound as crystals. $^1$H-NMR(CDCl$_3$) δppm:

11.53(1H, bs) 7.81(1H, d, J=1.1 Hz) 7.63(1H, d, J=1.7 Hz) 7.02(1H, dd, J=1.7, 3.9 Hz) 5.33(1H, t, J=4.9 Hz) 5.05(1H, ddd, J=2.8, 2.8, 3.9 Hz) 3.74(1H, ddd, J=2.8, 4.9, 12.6 Hz) 3.67(1H, ddd, J=2.8, 4.9, 12.6 Hz) 1.75(3H, d, J=1.1 Hz)

EXAMPLE 13

1-(2'-Cyano-2',3'-dideoxy-2',3'-didehydro-β-D-arabinofuranosyl)-N$^4$-acetylcytosine The procedures in Example 12 were analogously repeated using 70 mg of the compound of Reference example 4. After purification Over a silica gel column (φ1.8×7 cm) (eluted with methanol/chloroform=10:90), crystallization from ethanol-ether was carried out to obtain 14 mg of the title compound as crystals. $^1$H-NMR(DMSO-d$_6$) δppm:

11.02(1H, s) 8.33(1H, d, J=7.1 Hz) 7.65(1H, t, J=1.7 Hz) 7.24(1H, d, J=7.1 Hz) 7.12(1H, dd, J=1.7, 3.3 Hz) 5.30(1H, t, J=4.9 Hz) 5.12(1H, m) 3.74(1H, dd, J=3.3, 12.6 Hz) 3.67(1H, dd, J=3.3, 12.6 Hz) 2.12(3H, s)

EXAMPLE 14

N$^4$-Benzyloxycarbonylcytidine

In pyridine was dissolved 4.86 g of cytidine as much as possible, and the resulting solution was subjected to azeotropic distillation twice to remove the moisture content therefrom. To the residue was added 100 ml of pyridine, and 12.6 ml of trimethylchlorosilane was added to the resulting mixture under ice-cooling, followed by stirring for 30 minutes. 49 ml of carbobenzoxychloride (30 to 35% toluene solution) was dropwise added to the resulting mixture. After the mixture was stirred at room temperature, the mixture was left to stand overnight. To the mixture was added 40 ml of water and the resulting mixture was stirred for 1.5 hours. After addition of methylene chloride, the organic layer was separated and washed with a saturated aqueous sodium chloride. The organic layer was then dried over anhydrous magnesium sulfate and the solvent was evaporated. The residue was subjected to azeotropic distillation three times with toluene and ethanol to obtain 6.13 g of the title compound as a crystalline residue. $^1$H-NMR(270 MHz in d$_6$-DMSO) δppm:

8.40(1H, d, J=7.3 Hz), 7.31–7.55(5H, m), 7.02(1H, d, J=7.3 Hz), 5.77(1H, d, J=2.4 Hz), 5.19(2H, s), 3.88–3.99(3H, m)

EXAMPLE 15

3',5'-O-TIPDS-N$^4$-benzyloxycarbonylcytidine

In pyridine was dissolved 6.0 g of the compound of Example 14, and the resulting solution was subjected to azeotropic distillation twice to remove the moisture content therefrom. The residue was dissolved in 200 ml of pyridine, and 5.09 ml of 1,3-dichloro-1,1,3,3-tetraisopropyldisiloxane was added thereto, followed by stirring at room temperature. After the mixture was left to stand for 2 days, the solvents were evaporated. The residue was dissolved in methylene chloride, and the solution was washed successively with water, 0.5N hydrochloric acid, a saturated aqueous sodium chloride, a saturated aqueous sodium hydrogencarbonate and a saturated aqueous sodium chloride. The residue was dried over anhydrous sodium sulfate, and the solvent was evaporated to obtain 10.23 g of the title compound. $^1$H-NMR(270 MHz in d$_6$-DMSO) δppm:

10.83(1H, bs), 8.12(1H, d, J=7.8 Hz), 7.32–7.43(5H, m), 7.03(1H, d, J=7.3 Hz), 5.59(1H, s), 5.19(1H, s), 3.91–4.24(5H, m), 0.80–1.14(28H, m)

EXAMPLE 16

N$^4$-Benzyloxycarbonyl-1-(3,5-O-TIPDS-δ-D-erythropentofuran-2-urosyl)cytosine

To 70 ml of methylene chloride were added 13.16 g of pyridinium dichromate, 3.31 ml of acetic anhydride, 0.94 ml of pyridine and 2.5 g of cellite, and the resulting mixture was stirred for 40 minutes. Separately, 7.23 g of the compound of Example 15 was dissolved in 30 ml of methylene chloride, and the resulting solution was added to the above prepared mixture. After thus obtained mixture was stirred at room temperature for 5 hours, ethyl acetate was added thereto and methylene chloride was distilled off. The residue was dissolved in ethyl acetate and insolubles were filtered off. After the filtrate was washed with 1N hydrochloric acid, a saturated aqueous sodium chloride, a saturated aqueous sodium hydrogencarbonate and a saturated aqueous sodium chloride, the filtrate was dried over anhydrous magnesium sulfate. The solvent was distilled off and the residue was purified over silica gel chromatography (methylene chloride/methanol=99:1) to obtain 2.84 g of the title compound. $^1$H-NMR(270 MHz in d$_6$-DMSO) δppm:

10.98(1H, bs), 8.15(1H, d, J=7.3 Hz), 7.32–7.44(5H, m), 7.09(1H, d, J=7.3 Hz), 5.49(1H, s), 5.20(2H, s), 5.07 (1H, d, J=8.3.Hz), 3.95–4.04(3H, m), 0.92–1.12(28H, m)

EXAMPLE 17

N$^4$-Benzyloxycarbonyl-2'-cyano-3',5'-O-TIPDS-β-D-arabinofuranosyl-cytosine

In 25 ml of tetrahydrofuran was dissolved 2.71 g of the compound of Example 16, and 13 ml of water was added thereto, followed by stirring. To the resulting mixture was added 436 mg of sodium cyanide under ice-cooling. Then, 740 mg of sodium hydrogencarbonate was added to the mixture, followed by stirring at room temperature for 7 hours. After the mixture was left to stand in a refrigerator overnight, 217 mg of sodium cyanide was further added thereto. The resulting mixture was stirred at room temperature for 8 hours, and after the solvents were distilled off, the residue was dissolved in ethyl acetate. The solution was washed three times with a saturated aqueous sodium chloride and dried over anhydrous magnesium sulfate, followed by evaporation of the solvent. The residue was purified over silica gel chromatography (eluted with methylene chloride/methanol =99.25:0.75)) and crystallized from acetonitrile to obtain 392 mg of the title compound. $^1$H-NMR(270 MHz in d$_6$-DMSO) δppm:

11.00(1H, bs), 8.05(1H, d, J=7.3 Hz), 7.83(1H, bs), 7.33–7.44(5H, m), 7.13(1H, d, J=7.8 Hz), 5.93(1H, s), 5.21(2H, s), 3.93–4.33(4H, m), 0.96–1.07(28H, m)

EXAMPLE 18

N$^4$-Benzyloxycarbonyl-2'-cyano-deoxy-3',5'-O-TIPDS-β-D-arabinofuranosylcytosine In 8 ml of toluene was dissolved 0.40 g of the compound of Reference example 5, and to the resulting solution were added 13.4 mg of α,α'-azobisisobutyronitrile and 0.20 ml of tributyltin hydride in this order in a nitrogen gas stream, followed by stirring at 100° C. for 2 hours. The solvent was distilled off and the residue was purified over silica gel chromatography (eluted with methylene chloride/methanol =99:1) to obtain 202 mg of the title compound. $^1$H-NMR (270 MHz in d$_6$-DMSO) δppm:

10.96(1H, bs), 8.02(1H, d, J=7.3 Hz), 7.32–7.44(5H, m), 7.12(1H, d, J=7.8 Hz), 6.20(1H, d, J=7.8 Hz), 5.20(2H, s), 3.91–4.72(5H, m), 0.95–1.23(28H, m)

EXAMPLE 19

N$^4$-Benzyloxycarbonyl-2'-cyano-2'-deoxy-β-D-arabinofuranosylcytosine

In 5 ml of tetrahydrofuran was dissolved 192 mg of the compound of Example 18, and after the resulting solution was ice-cooled in a nitrogen gas stream, a solution of 0.02 ml of acetic acid and 168 mg of tetrabutylammonium fluoride dissolved in 1.2 ml of tetrahydrofuran was added thereto, followed by stirring under ice-cooling for 2 hours. The solvents were distilled off and the residue was purified over silica gel chromatography (eluted with methylene chloride/methanol =95:5) to obtain 94 mg of the title compound. $^1$H-NMR(270 MHz in $d_6$-DMSO) δppm:

10.92(1H, bs), 8.36(1H, d, J=7.3 Hz), 7.34–7.44(5H, m), 7.11(1H, d, J=7.8 Hz), 6.25(1H, d, J=5.4 Hz), 6.20(1H, d, J=6.8 Hz), 5.24(1M, d, J=4.4 Hz), 5.20(2H, s), 4.43(1H, q, J=7.3, 12.7 Hz), 3.61–3.93(4H, m)

EXAMPLE 20

2'-Cyano-2',3'-dideoxy-2',3'-didehydro-β-D-ribofuranosylcytosine

The synthetic procedures for the compound of Example 12 was analogously repeated using 300 mg of the compound of Example 8 to obtain 60 mg of the title compound. $^1$H-NMR(270 MHz in $d_6$-DMSO) δppm:

7.79(1H, d, J=7.3 Hz), 7.55–7.56(1H, m), 7.36(2H, d, J=7.3 Hz), 7.07(1H, dd, J=1.96, 3.90 Hz), 5.78(1H, d, J=7.3 Hz), 5.18–5.21(1H, m), 5.01–5.03(1H, m), 3.65–3.70(2H, m)

REFERENCE EXAMPLE 1

1-[2'-Cyano-2'-deoxy-5'-O-(4,4'-dimethoxytriphenylmethyl)-β-D-arabinofuranosyl] thymine In 7 ml of anhydrous pyridine was dissolved 267 mg of the compound of Example 3 and to the resulting solution was added 508 mg of 4,4'-dimethoxytriphenylmethyl chloride, followed by stirring at room temperature for 1.5 hours in an argon gas stream. After completion of the reaction, the solvent was distilled off, and 100 ml of ethyl acetate was added to the residue. After the mixture was washed three times with 50 ml of water and dried over anhydrous sodium sulfate, the solvent was evaporated. The residue was purified over a silica gel column (φ1.8×8.5 cm) (eluted with ethanol/chloroform=1-2:99-88) to obtain 574 mg of the title compound as a yellowish white foam. $^1$H-NMR(CDCl$_3$) δppm:

8.40(1H, bs) 7.50(1H, d, J=1.2 Hz) 4.77–7.26(9H, m) 6.90-6.80(4H, m) 6.27(1H, d, J=6.8 Hz) 4.74(1H, d, J=6.8 Hz) 3.93(1H, m) 3.79(6H, s) 3.62(1H, m) 3.61 (1H, m) 3.30(2H, m) 1.67(1H, d, J=1.2 Hz)

REFERENCE EXAMPLE 2

1-[2'-Cyano-2'-deoxy-5'-O-(4,4'-dimethoxytriphenylmethyl)-β-D-arabinofuranosyl]-N$^4$-acetylcytosine The procedures in Reference Example 1 were repeated analogously using 194 mg of the compound of Example 7 to obtain 326 mg of the title compound as a yellowish white foam. $^1$H-NMR(CDCl$_3$) δppm:

8.80(1H, bs) 8.19(1H, d, J=7.6 Hz) 7.41-7.14 and 6.89-6.76(14H, m) 6.30(1H, d, J=6.1 Hz) 4.79(2H, m) 4.08(2H, m) 3.79(6H, s) 3.56(2H, m) 2.09(3H, s)

REFERENCE EXAMPLE 3

1-[2'-Cyano-2',3'-dideoxy-2',3'-didehydro-5'-O-(4,4'-dimethoxytriphenylmethyl)-β-D-ribofuranosyl] thymine In 3 ml of anhydrous dimethylformamide was dissolved 200 mg of the compound of Reference example 1, and to the resulting solution was added 94 mg of thiocarbonyldiimidazole, followed by stirring at room temperature for 13 hours and 40 minutes in an argon gas stream. After completion of the reaction, ethyl acetate was added to the reaction mixture, and the mixture was washed three times with water and dried over anhydrous sodium sulfate, followed by evaporation of the solvents. The residue was purified over a silica gel column (2φ×6.5 cm) (eluted with hexane/ethyl acetate=1:1 to 1:2) to obtain 162 mg of the title compound as a white caramel. $^1$H-NMR(CDCl$_3$) δppm:

8.40(1H, bs) 7.45(1H, d, J=1.1 Hz) 7.10(1H, d, J=1.8 Hz) 7.06(1H, dd, J=1.8, 4.0 Hz) 5.10(1H, ddd, J=2.6, 3.3, 4.0 Hz) 4.12(3H, s) 3.61(1H, dd, J=2.6, 11.0 Hz) 3.45(1H, dd, J=3.3, 11.0 Hz) 1.90(3H, d, J=1.1 Hz)

REFERENCE EXAMPLE 4

1-[2'-Cyano-2',3'-dideoxy-2',3'-didehydro-5'-O-(4,4'-dimethoxytriphenylmethyl)-β-D-arabinofuranosyl]-N$^4$-acetylcytosine The procedures in Reference example 3 were repeated analogously using 326 mg of the compound of Reference example 2, and after purification, crystallization from ether was carried out to obtain 163 mg of the title compound as crystals. $^1$H-NMR(DMSO-$d_6$) δppm:

9.22(1H, s) 8.16(1H, d, J=7.3 Hz) 7.35-7.22(9H, m) 6.95(1H, dd, J=1.8, 4.0 Hz) 6.90-6.84(5H, m) 6.68(1H, dt, J=1.8) 5.08(1H, ddd, J=2.6, 2.9, 4.0 Hz) 3.82(6H, s) 3.71(1H, dd, J=2.9, 11.7 Hz) 3.59(1H, dd, J=2.6, 11.7 Hz) 2.24(3H, s)

REFERENCE EXAMPLE 5

N$^4$-Benzyloxycarbonyl-2'-cyano-2'-phenoxythiocarbonyl-3',5'-O-TIPDS-β-D-arabinofuranosyl-cytosine In pyridine was dissolved 525 mg of the compound of Example 17, and after the moisture content was removed by azeotropic distillation, the residue was dissolved in 5 ml of methylene chloride. To the resulting solution were added 40 mg of dimethylaminopyridine, 0.17 ml of phenyl chlorothionoformate and 0.17 ml of triethylamine in this order under ice-cooling in a nitrogen gas stream, and the mixture was stirred for 4 hours under ice-cooling. Methylene chloride was added to the reaction mixture, and after the resulting mixture was washed with a saturated aqueous sodium chloride, 0.1N hydrochloric acid and a saturated aqueous sodium chloride and dried over anhydrous magnesium sulfate, the solvents were evaporated. The residue was purified over silica gel chromatography (eluted with methylene chloride/methanol=99.5:0.5) to obtain 0.46 g of the title compound. $^1$H-NMR(270 MHz in $d_6$-DMSO) δppm:

11.02(1H, bs), 8.00(1H, d, J=7.8 Hz), 7.31–7.98(10H, m), 7.11(1H, d, J=7.8 Hz), 6.29(1H, s), 5.75(1H, bs), 5.20 (2H, s), 3.98–4.17(3H, m), 1.00–1.12(28H, m)

Preparation Example 1 Hard capsules

In each piece of standard cap-and-body type hard gelatin capsules were charged 100 mg of the powdery complex of Example 1, 150 mg of lactose, 50 mg of cellulose and 6 mg of magnesium stearate to prepare unit capsules. The thus obtained capsules were washed and dried to provide hard capsule preparations.

Preparation Example 2 Tablets

Tablets were prepared by mixing 100 mg of the complex of Example 1, 0.2 g of colloidal silicon dioxide, 5 mg of magnesium stearate, 275 mg of microcrystalline cellulose, 11 mg of starch and 98.8 mg of lactose, and pelletizing the mixture.

Incidentally, coating was applied to the tablets, if desired.

Preparation Example 3 Injections

In 10% by volume of propylene glycol was stirred 1.5 % by weight of the complex of Example 1. The mixture was then made to a predetermined volume with a distilled water for injection, followed by serialization to obtain an injection.

Preparation Example 4 Suspension

To 5 ml were admixed 100 mg of the micropowdery complex of Example 1, 100 mg of sodium carboxymethyl cellulose, 5 mg of sodium benzoate, 1.0 g of sorbitol solution (The Pharmacopoeia of Japan) and 0.025 ml of vaniline, followed by homogeneous suspending to obtain a suspension.

Effect of the Invention

Test Example

1. Evaluation of antitumor activity in vitro

Antitumor activity was determined in vitro using a human cancer strain. As the culture medium for the cancer cell, an RPMI1640 solution containing 10% of immobilized bovine fetal serum 50 μg/ml of kanamycin was used. Cancer cells ($1 \times 10^4$ cells/ml) were innoculated to 1 ml of the culture liquids containing samples at different concentrations, respectively, and cultured in a carbon dioxide gas incubator at 37° C. for 72 hours.

Viability of the cancer cells was determined by MTT method in which the amount of living cells in the culture liquids containing the sample and that in culture liquids containing no sample (blank group) are measured based on the intensity of the visible light using [3-(4,5-dimethylthiazol-2-yl)-2,5-diphenyl-tetrazolium bromide] which develops color in proportion to the number of living cells. The intensity of antitumor activity was expressed by $IC_{50}$ value (concentration (μg/ml) necessary for inhibiting proliferation of the cells to 50%). The $IC_{50}$ value was obtained from a graph illustrating the relationship between % proliferation of the cancer cells in the sample containing group (% relative to the blank group) and the concentration (logarithmic) of the sample.

The results are summarized in Table 4.

TABLE 4

Antitumor activity in vitro

| Compound No. | $IC_{50}$ (μg/ml) | |
|---|---|---|
| | L1210 | K B |
| Example 9 | 0.21 | 15 |
| Example 12 | 3.1 | 7.6 |

L1210: Mouse leukemia cell
KB: human oral epidermoid carcinoma

Industrial utilizability

Compounds (1) and (2) of the present invention exhibit strong antitumor activities to P388 cell transplanted to a mouse and to various human cancers. They can be absorbed well by oral administration and have low toxicity with mild side effects. Accordingly, they are very useful for treatment or prophylaxis of tumorgenic diseases as novel pyrimidine nucleoside type antitumor agents. In addition, Compounds (1) and (2) of the present invention are very useful as intermediates for producing excellent antitumor agents. The pyrimidine nucleoside derivatives of the present invention can be administered to warm-blooded animals including human being. The administration form includes intravenous injections, subcutaneous injections, intramuscular injections and suppositories for parenteral administration, and tablets, capsules, powders and granules for oral administration.

While the dose for adult varies depending on the disease to be treated, administration route, number of dosages and administration period, the preparation is administered in an amount of 0.01 to 5 g per day once or in several portions.

Further, the present compounds can be used in combination with other antitumor agents such as nitrosourea drugs, e.g. 5Fu, AraC, ACNU and BCNU, cisplatin, daunomycin, adriamycin, mitomycin C or etoposide. In addition, the pyrimidine nucleoside derivative can be prepared into desired administration forms using arbitrarily conventional methods. The present invention therefore includes pharmaceutical preparations and compositions containing pharmaceutically acceptable pyrimidine nucleoside derivatives.

The composition for injection is provided in unit dosage ampuls or multiple-dosage containers. The composition may contain additives such as suspending agents, stabilizers and dispersing agents, and usually is a powder which is redissolved before use in an appropriate solvent such as a sterilized aqueous medium containing no pyrogenic material. Such preparation can be prepared, for example, by dissolving a pyrimidine nucleoside derivative in acetone, pouring in vials and freeze-drying after addition of water. Further, the compositions for oral administration can be provided in the form of tablets, capsules, powders, granules and syrups containing suitable amounts of pyrimidine nucleoside derivatives for administration.

We claim:

1. A process for preparing a compound of the formula:

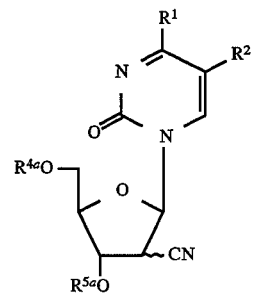

wherein $R^1$ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1$–$C_4$ alkyl, an alkenyloxycarbonyl having a $C_2$–$C_4$ alkenyl and an aralkyloxycarbonyl having 8 to 12 carbon atoms which optionally has a substituent on the ring;

$R^2$ represents a hydrogen atom or an alkyl group having 1 to 4 carbon atoms; and $R^{4a}$ and $R^{5a}$ together represent a group of the formula: 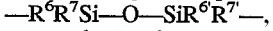—$R^6R^7Si$—O—$SiR^{6'}R^{7'}$—, wherein $R^6$, $R^7$, $R^{6'}$ and $R^{7'}$ are the same or different from one another and each represent an alkyl group having 1 to 4 carbon atoms, which process comprises reacting a reducing agent and a cyanolating agent with a compound of the formula:

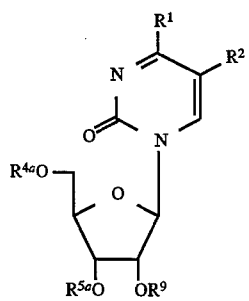

wherein $R^1$, $R^2$, $R^{4a}$ and $R^{5a}$ have the same meanings as defined above; and $R^9$ represents an alkoxythiocarbonyl group having a $C_1-C_4$ alkyl or an arylthiocarbonyl group having a $C_6-C_{10}$ aryl.

2. A process for preparing a compound of the formula:

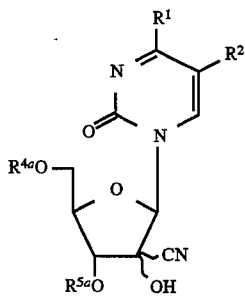

wherein $R^1$ represents a hydroxyl group or an amino group which is unsubstituted or substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1-C_4$ alkyl, an alkenyloxycarbonyl having a $C_2-C_4$ alkenyl, and an aralkyloxycarbonyl having 8 to 12 carbon atoms which optionally has a substituent on the ring;

$R^2$ represents a hydrogen atom or an alkyl group having 1 to 4 carbon atoms; and $R^{4a}$ and $R^{5a}$ together represent a group of the formula: $—R^6R^7Si—O—SiR^{6'}R^{7'}—$, wherein $R^6$, $R^7$, $R^{6'}$ and $R^{7'}$ are the same or different from one another and represent an alkyl group having 1 to 4 carbon atoms, which process comprises reacting a cyanolating agent with a compound of the formula:

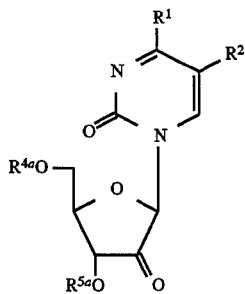

wherein $R^1$, $R^2$, $R^{4a}$ and $R^{5a}$ have the same meanings as defined above.

3. A process for preparing a compound of the formula:

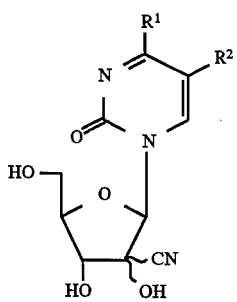

wherein $R^1$ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1-C_4$ alkyl, an alkenyloxycarbonyl having a $C_2-C_4$ alkenyl and an aralkyloxycarbonyl having 8 to 12 carbon atoms which optionally has a substituent on the ring;

$R^2$ represents a hydrogen atom or an alkyl group having 1 to 4 carbon atoms, which process comprises reacting a deprotecting agent with a compound of the formula:

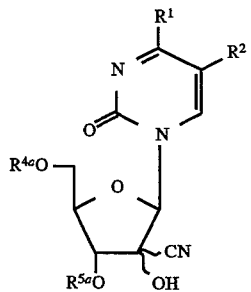

wherein $R^1$ and $R^2$ have the same meanings as defined above; and $R^{4a}$ and $R^{5a}$ together represent a group of formula: $—R^6R^7Si—O—SiR^{6'}R^{7'}—$, wherein $R^6$, $R^7$, $R^{6'}$ and $R^{7'}$ are the same or different from one another and represent an alkyl group having 1 to 4 carbon atoms.

4. The process according to claim 3, wherein the compound prepared by the process is selected from the group consisting of 1-(2'-cyano-β-D-arabinofuranosyl)cytosine, 1-(2'-cyano-β-D-arabinofuranosyl)uracil, 1-(2'-cyano-β-D-arabinofuranosyl)thymine, 1-(2'-cyano-β-D-ribofuranosyl)cytosine, 1-(2'-cyano-β-D-ribofuranosyl)uracil and 1-(2'-cyano-β-D-ribofuranosyl)thymine.

5. A process for preparing a compound of the formula:

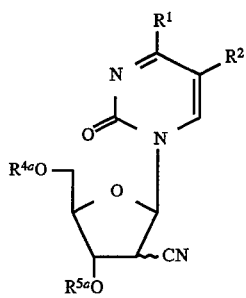

wherein $R^1$ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1$–$C_4$ alkyl, an alkenyloxycarbonyl having a $C_2$–$C_4$ alkenyl, and an aralkyloxycarbonyl having 8 to 12 carbon atoms which optionally has a substituent on the ring;

$R^2$ represents a hydrogen atom or an alkyl group having 1 to 4 carbon atoms; and $R^{4a}$ and $R^{5a}$ together represent a group of formula: —$R^6R^7Si$—O—$SiR^{6'}R^{7'}$—, wherein in $R^6$, $R^7$, $R^{6'}$ and $R^{7'}$ are the same or different from one another and represent an alkyl group having 1 to 4 carbon atoms, which process comprises reacting a reducing agent with a compound of the formula:

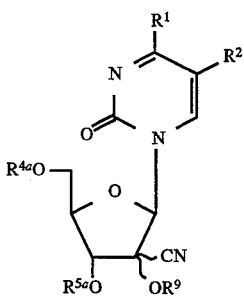

wherein $R^1$, $R^2$, $R^{4a}$ and $R^{5a}$ have the same meanings as defined above; and $R^9$ represents an alkoxythiocarbonyl group having a $C_1$–$C_4$ alkyl or an arylthiocarbonyl group having a $C_6$–$C_{10}$ aryl.

6. A process for preparing a compound of the formula:

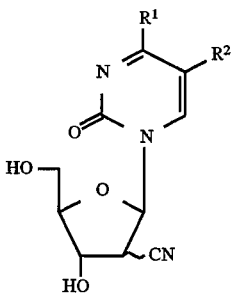

wherein $R^1$ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1$–$C_4$ alkyl, an alkenyloxycarbonyl having a $C_2$–$C_4$ alkenyl, and an aralkyloxycarbonyl having 8 to 12 carbon atoms which optionally has a substituent on the ring;

which process comprises reacting a deprotecting agent with a compound of the formula:

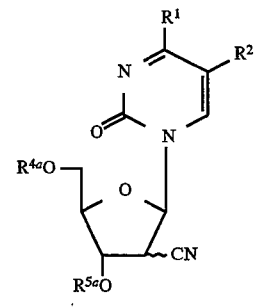

wherein $R^1$ and $R^2$ have the same meanings as defined above; and $R^{4a}$ and $R^{5a}$ together represent a group of formula: —$R^6R^7Si$—O—$SiR^{6'}R^{7'}$—, wherein $R^6$, $R^7$, $R^{6'}$ and $R^{7'}$ are the same or different from one another and each represent an alkyl group having 1 to 4 carbon atoms.

7. The process according to claim 6, wherein the compound prepared by the process is selected from the group consisting of 1-(2'-cyano-β-D-2'-deoxy-arabinofuranosyl)cytosine,
1-(2'-cyano-β-D-2'-deoxy-arabinofuranosyl)uracil,
1-(2'-cyano-β-D-2'-deoxy-arabinofuranosyl)thymine,
1-(2'-cyano-β-D-2'-deoxy-ribofuranosyl)cytosine,
1-(2'-cyano-β-D-2'-deoxy-ribofuranosyl)uracil and
1-(2'-cyano-β-D-2'-deoxy-ribofuranosyl)thymine.

8. A process for preparing a compound of the formula:

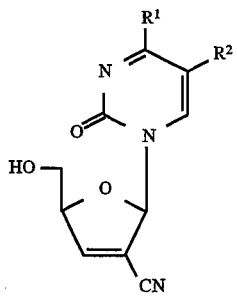

wherein $R^1$ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1$–$C_4$ alkyl, an alkenyloxycarbonyl having a $C_2$–$C_4$ alkenyl, and an aralkyloxycarbonyl having 8 to 12 carbon atoms which optionally has a substituent on the ring;

which process comprises reacting a deprotecting agent for a protective group of the 5-position hydroxyl group with a compound of the formula:

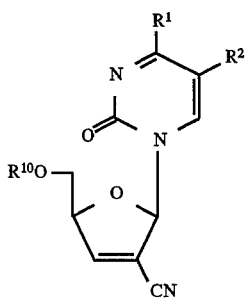

wherein R¹ and R² have the same meanings as defined above; and $R^{10}$ represents a protective group for a hydroxyl group.

9. The process according to claim 8, wherein the compound prepared by the process is selected from the group consisting of 1-(2'-cyano-β-D-2',3'-didehydro-2',3'-deoxyribofuranosylcytosine, 1-(2'-cyano-β-D-2',3'-didehydro-2', 3'-deoxyribofuranosyluracil, and 1-(2'-cyano-β-D-2',3'-didehydro-2',3'-deoxyribofuranosylthymine.

10. A process for preparing a compound of the formula:

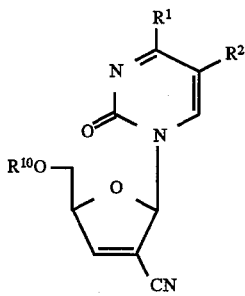

wherein R¹ represents a hydroxyl group or an amino group which is unsubstituted or which is substituted by a substituent selected from the group consisting of an aliphatic acyl having 1 to 4 carbon atoms, an aromatic acyl having 7 to 11 carbon atoms which optionally has a substituent on the ring, an alkoxycarbonyl having a $C_1$–$C_4$ alkyl, an alkenyloxycarbonyl having a $C_2$–$C_4$ alkenyl, and an aralkyloxycarbonyl having 8 to 12 carbon atoms which optionally has a substituent on the ring;

which process comprises reacting an alkoxythiocarbonyl halide having a $C_1$–$C_4$ alkyl, an arylthiocarboxyl halide having a $C_6$–$C_{10}$ aryl or a thiocarbonyldiimidazole with a compound of the formula:

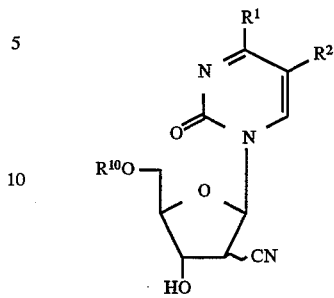

wherein R¹, R² and $R^{10}$ have the same meanings as defined above.

11. The process according to claim 1 wherein the reacting is carried out at a temperature of 50° C. to 250° C. for 30 minutes to 12 hours.

12. The process according to claim 1 wherein the reacting is carried out at a temperature of 80° C. to 150° C. for 1 hour to 5 hours.

13. The process according to claim 2 wherein the reacting is carried out at a temperature of 0° C. to 100° C. for 30 minutes to 96 hours and the cyanolating agent is a cyanide of an alkali metal.

14. The process according to claim 2 wherein the reacting is carried out at a temperature of 10° C. to 40° C. for 5 hours to 24 hours and the cyanolating agent is selected from the group consisting of sodium cyanide and potassium cyanate.

15. The process according to claim 3 wherein the reacting is carried out at a temperature of 0° C. to 40° C. for 10 minutes to 24 hours.

16. The process according to claim 5 wherein the reacting is carried out at a temperature of 50° C. to 250° C. for 30 minutes to 10 hours.

17. The process according to claim 6 wherein the reacting is carried out at a temperature of 0° C. to 40° C. for 10 minutes to 24 hours.

18. The process according to claim 8 wherein the reacting is carried out at a temperature of –10° C. to 50° C. for 1 hour to 24 hours.

19. The process according to claim 10 wherein the reacting is carried out at a temperature of –10° C. to 50° C. for 1 hour to 24 hours in the presence of thiocarbonyl diimidazole or phenoxythiocarbonyl chloride.

* * * * *

UNITED STATES PATENT AND TRADEMARK OFFICE
CERTIFICATE OF CORRECTION

PATENT NO. : 5,654,420
DATED : August 5, 1997
INVENTOR(S) : MATSUDA et al

It is certified that error appears in the above-identified patent and that said Letters Patent is hereby corrected as shown below:

Title Page, Left Column, [62] Related U.S. Application Data:

Division of Ser. No.301,720, Sep. 7, 1994, Pat. No.5,616,567, which is a continuation of Ser. No. 989,719, Dec. 14, 1992, which is a continuation of PCT/JP91/00797, Jun. 13, 1991.--.

Signed and Sealed this

Twenty-eighth Day of December, 1999

Attest:

Q. TODD DICKINSON

Attesting Officer

Acting Commissioner of Patents and Trademarks